United States Patent
Shiflett et al.

(10) Patent No.: US 7,964,760 B2
(45) Date of Patent: *Jun. 21, 2011

(54) PROCESS FOR THE SEPARATION OF FLUOROCARBONS USING IONIC LIQUIDS

(75) Inventors: Mark Brandon Shiflett, Wilmington, DE (US); Akimichi Yokozeki, Wilmington, DE (US); Jeffrey P. Knapp, Wilmington, DE (US)

(73) Assignee: E.I. du Pont de Nemours and Company, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 12/124,441

(22) Filed: May 21, 2008

(65) Prior Publication Data

US 2008/0293978 A1    Nov. 27, 2008

Related U.S. Application Data

(60) Provisional application No. 60/940,292, filed on May 25, 2007.

(51) Int. Cl.
C07C 17/38    (2006.01)

(52) U.S. Cl. .......................... 570/180; 570/263

(58) Field of Classification Search .................. None
See application file for complete search history.

(56) References Cited

U.S. PATENT DOCUMENTS

| | | | |
|---|---|---|---|
| 4,234,544 A | 11/1980 | Christman | |
| 5,340,555 A | 8/1994 | Mashio | |
| 5,470,442 A | 11/1995 | Mahler et al. | |
| 5,698,750 A | 12/1997 | Mouk | |
| 5,709,092 A | 1/1998 | Shiflett | |
| 6,139,747 A | 10/2000 | Rotzheim | |
| 6,579,343 B2 | 6/2003 | Brennecke | |
| 6,843,934 B2 | 1/2005 | Bement | |
| 7,435,318 B2 | 10/2008 | Arlt et al. | |
| 2002/0001560 A1 | 1/2002 | Miller | |
| 2004/0035293 A1 | 2/2004 | Davis | |
| 2004/0133058 A1 | 7/2004 | Arlt et al. | |
| 2006/0197053 A1 | 9/2006 | Shiflett | |
| 2006/0272934 A1 | 12/2006 | Beste | |
| 2007/0019708 A1 | 1/2007 | Shiflett | |
| 2007/0144186 A1 | 1/2007 | Shiflett | |
| 2007/0080052 A1 | 4/2007 | Beste | |
| 2007/0131535 A1* | 6/2007 | Shiflett et al. | 203/50 |
| 2007/0295478 A1 | 12/2007 | Shiflett | |
| 2007/0297965 A1 | 12/2007 | Shiflett | |
| 2008/0028777 A1 | 2/2008 | Boesmann | |
| 2008/0153697 A1 | 6/2008 | Shiflett | |
| 2008/0293978 A1 | 11/2008 | Shiflett | |

(Continued)

FOREIGN PATENT DOCUMENTS

WO    2007038363    * 4/2007

(Continued)

OTHER PUBLICATIONS

Shiflett et al., Ind. Eng. Chem. Res., 2006, 45 (18), pp. 6375-6382.*

(Continued)

*Primary Examiner* — Karl J Puttlitz (57) ABSTRACT

This invention relates to a process for separating 1,1,2,2-tetrafluoroethane or 1,1,1,2-tetrafluoroethane from a mixture comprising both 1,1,1,2-tetrafluoroethane and 1,1,2,2-tetrafluoroethane wherein at least one ionic liquid is used to enhance the efficiency of the separation.

19 Claims, 2 Drawing Sheets

A schematic diagram of a simple extractive distillation system

U.S. PATENT DOCUMENTS

2009/0030235 A1   1/2009   Jakel
2009/0131728 A1   5/2009   Shiflett
2010/0144994 A1   6/2010   Shiflett

FOREIGN PATENT DOCUMENTS

WO   WO2007/038363 A2   4/2007

OTHER PUBLICATIONS

Seddon, Ionic Liquids for Clean Technology, J. Chem. Tech. Biotechnol., 1997, vol. 68:351-356.
Olivier et al., Nonaqueous Room-Temperature Ionic Liquids: A New Class of Solvents for Catalytic Organic Reactions, Chem. Ind., 1996, vol. 68:249-263.
John E. Enderby, Ionic Liquids: Recent Progress and Remaining Problems, J. Phys. Condensed Matter, 1993, vol. 5:99-106.
M. Freemantle, Designer Solvents, Ionic Liquids May Boost Clean Technology Development, Chemical and Engineering News, Mar. 30, 1998, pp. 32-37.
Gordon et al., Ionic Liquid Crystals: Hexafluorophosphate Salts, J. Mater. Chem., 1998, vol. 8:2627-2636.
Welton, Room-Temperature Ionic Liquids, Solvents for Synthesis and Catalysis, Chem. Rev., 1999, vol. 99:2071-2084.
Perry's Chemical Engineers Handbook, 7th Edition, 1997, McGraw-Hill (Book Not Included).
Heat Transfer, Kirk-Othmer Encyclopedia of Chemical Technology, 5th Edition, 2005, vol. 13:242-281, John Wiley & Sons.
M. B. Shiflett et al., Solubilities and Diffusivities of Carbon Dioxide in Ionic Liquids: [bmim] [PF6] and [BF4], Ind. Eng. Chem. Res., 2005, vol. 44:4453-4464.
S. I. Sandler, Chemical and Engineering Thermodynamics, Chemical and Engineering Thermodynamics, 3rd Edition, 1999, John Wiley & Sons.
M. B. Shiflett et al., Solubility and Diffusivity of Hydrofluorocarbons in Room-Temperature Ionic Liquids, Aiche J., 2006, vol. 52:1205.
U.S. Appl. No. 11/525,466, filed Sep. 22, 2006, Mark Brandon Shiflett.
M. B. Shiflett, Solubility Differences of Halocarbo Isomers in Ionic Liquid, J. Chem. Eng. Data, 2007, vol. 52, pp. 2007-2015.
International Search Report Dated Sep. 12, 2008.

* cited by examiner

Figure 1 – A schematic diagram of a simple extractive distillation system

Figure 2. Process Schematic

PROCESS FOR THE SEPARATION OF FLUOROCARBONS USING IONIC LIQUIDS

This application claims the benefit of U.S. Provisional Application No. 60/940,292, filed 25 May 2007, which is by this reference incorporated in its entirety as a part hereof for all purposes.

TECHNICAL FIELD

This invention relates to a process for separating various isomers of a compound that are contained together in the same mixture. In particular, this invention relates to a process for separating 1,1,2,2-tetrafluoroethane or 1,1,1,2-tetrafluoroethane from a mixture containing both 1,1,1,2-tetrafluoroethane and 1,1,2,2-tetrafluoroethane wherein at least one ionic liquid is used to enhance the efficiency of the separation.

BACKGROUND 1,1,1,2-Tetrafluoroethane, $CF_3CH_2F$ (also known as HFC-134a, F-134a, or R-134a), can be used as a refrigerant, an aerosol propellant, a heat transfer medium, a gaseous dielectric, a fire extinguishing agent, an expansion agent for polyolefins and polyurethanes, a fluid for absorption cooling systems, and a power cycle working fluid. R-134a is nonflammable, has no ozone depletion potential, and has low global warming potential. It is therefore suited as a replacement for chlorine-containing gases, such as chlorofluorocarbons and hydrochlorofluorocarbons, that are believed to be involved in ozone depletion.

Depending on the operating conditions under which R-134a is made, 1,1,2,2-tetrafluoroethane, $CHF_2CHF_2$ (also known as HFC-134, F-134, or R-134), can also be made as a product of the synthesis. R-134 and R-134a may be obtained from a variety of different manufacturing processes or sources. For example, a mixture containing R-134 and R-134a can be produced by reacting a mixture containing $CF_3CCl_3$ (R-113a) and $CCl_2FCClF_2$ (R-113) with hydrogen fluoride to produce a mixture containing $CCl_2FCF_3$ (R-114a) and $CClF_2CClF_2$ (R-114). The mixture containing R-114a and R-114 is then hydrogenated under appropriate conditions to produce a mixture of R-134a and R-134. This mixture containing R-134a and R-134 can also contain impurities, such as $CClHFCF_3$ (R-124), $CHF_2CClF_2$ (R-124a) and unreacted R-114 and R-114a.

R-134 is also useful as a refrigerant, and for other applications as described above for R-134a. R-134 and R-134a are, however, difficult to separate because they have similar boiling points—the normal boiling point of R-134 being −19.6° C. and the normal boiling point of R-134a being −26.1° C. These close boiling points make efficient separation of R-134 and R-134 by conventional distillation extremely difficult because of the tendency of those components to form an azeotrope, azeotropic composition or an azeotrope-like composition in a mixture. In order to achieve separation by conventional distillation, impracticably tall columns would have to be operated at high reflux ratios, which would likely result in high capital and operating costs, and possibly also in substantial yield loss of the product.

U.S. Pat. No. 5,470,442 discloses a method for separating R-134 and R-134a from each other, and/or from fluorocarbon impurities, by extractive distillation where an alcohol is used as the extractive agent. U.S. application Ser. No. 11/525,466, which by this reference is incorporated in its entirety as a part hereof for all purposes, describes the use of ionic liquids in separation processes to separate components of mixtures.

Despite these existing separation processes, a need still remains for a separation process better suited to the objective of separating R-134 and R-134a from each other.

SUMMARY

In one embodiment, this invention relates to a process for separating 1,1,2,2-tetrafluoroethane from a mixture that contains both 1,1,2,2-tetrafluoroethane and 1,1,1,2-tetrafluoroethane, by contacting the mixture with at least one ionic liquid in which 1,1,1,2-tetrafluoroethane is soluble to a greater extent than 1,1,2,2-tetrafluoroethane and separating 1,1,2,2-tetrafluoroethane from the mixture.

In another embodiment, this invention relates to a process for separating 1,1,1,2-tetrafluoroethane from a mixture that contains both 1,1,2,2-tetrafluoroethane and 1,1,1,2-tetrafluoroethane, by contacting the mixture with at least one ionic liquid in which 1,1,2,2-tetrafluoroethane is soluble to a greater extent than 1,1,1,2-tetrafluoroethane and separating 1,1,1,2-tetrafluoroethane from the mixture.

In a further embodiment, the processes of this invention may be conveniently performed by contacting the mixture of 1,1,2,2-tetrafluoroethane and 1,1,1,2-tetrafluoroethane with an ionic liquid in a distillation column.

DETAILED DESCRIPTION

This invention relates to a process for separating either 1,1,2,2-tetrafluoroethane (R-134) or 1,1,1,2-tetrafluoroethane (R-134a) from a mixture that contains both isomers of the compound, wherein at least one ionic liquid is used to increase the efficiency of the separation. An ionic liquid is well suited for use for this purpose since it exhibits negligible volatility and is not flammable. If R-134 is to be separated from the mixture, the mixture of R-134 and R-134a is contacted with at least one ionic liquid in which R-134a is soluble to a greater extent than R-134, and R-134 is then separated from the mixture. Conversely, if R-134a is to be separated from the mixture, the mixture of R-134 and R-134a is contacted with at least one ionic liquid in which R-134 is soluble to a greater extent than R-134a, and R-134a is then separated from the mixture.

In the description of this invention, the following definitional structure is provided for certain terminology as employed variously in the specification:

An "alkane" or "alkane compound" is a saturated hydrocarbon compound that has the general formula $C_nH_{2n+2}$, and that may be a straight-chain, branched or cyclic compound.

An "alkene" or "alkene compound" is an unsaturated hydrocarbon compound that contains one or more carbon-carbon double bonds, and that may be a straight-chain, branched or cyclic compound. An alkene requires a minimum of two carbons. A cyclic compound requires a minimum of three carbons.

An "aromatic" or "aromatic compound" includes benzene and compounds that resemble benzene in chemical behavior.

An "azeotrope" or "azeotropic composition" is a constant-boiling mixture of two or more substances that behaves as a single substance with respect to the fact that the vapor produced by partial evaporation or distillation of the liquid of the azeotrope has the same composition as the liquid from which it is evaporated or distilled, i.e. the mixture distills/refluxes without compositional change. Constant-boiling compositions are characterized as azeotropic because they exhibit either a maximum or minimum boiling point as compared with that of the non-azeotropic mixture of the same components. Azeotropic compositions are also characterized by a minimum or a maximum in the vapor pressure relative to the vapor pressure as a function of composition at a constant temperature.

An "azeotrope-like composition" is a composition that has a constant-boiling characteristic, or a tendency not to fractionate upon boiling or evaporation. Therefore, the composition of the vapor formed is the same as, or substantially the same as, the original liquid composition. During boiling or evaporation, the liquid composition, if it changes at all, changes to only a minimal or negligible extent. An azeotrope-like composition can also be characterized by the area that is adjacent to the maximum or minimum vapor pressure in a plot of composition vapor pressure at a given temperature as a function of mole fraction of components in the composition. A composition is azeotrope-like if, after about 50 weight percent of an original composition is evaporated or boiled off to produce a remaining composition, the change between the original composition and the remaining composition is no more than about 6 weight %, and often is no more than about 3 weight %, relative to the original composition.

An azeptrope, azeotropic composition or azeotrope-like composition may also be characterized as a close-boiling, substantially constant-boiling or constant-boiling mixture that may appear under many guises, depending upon the existing conditions, as illustrated by the manner in which the following factors may apply:

1) At different pressures, the compositional content of these kinds of mixture will vary to at least some degree, as will the boiling point temperature. Thus, such a mixture represents a unique type of relationship between the components thereof, but will typically have variable compositional content, which depends on temperature and/or pressure. Therefore, ranges of compositional content, rather than a fixed compositional content, are often used to define such a mixture.
2) These kinds of mixtures can be characterized by a boiling point at a given pressure rather than by a specific compositional content, the determination of which is limited by, and is only accurate as, the analytical equipment available to make the determination.
3) Both the boiling point and the weight (or mole) percent content of each component in these kinds of mixtures may change when the mixture is allowed to boil at different pressures. Thus, such a mixture may be defined in terms of the unique relationship that exists among the components thereof, or in terms of the exact weight (or mole) percentages of each component therein in terms of a fixed boiling point at a specific pressure.

An "extractant" is a compound such as a solvent that, when added to a mixture, interacts with the components of that mixture in a way that changes the relative volatilities of at least two of the components such that those components may then be more easily separated from each other. An extractant, when used herein, is used in an "effective amount", which is an amount that, when added to a mixture of components, causes the volatility of one component to increase relative to the volatility of the other component to allow the separation of the more volatile component from the mixture.

"Extractive distillation" is a process in which an extractant is added to the components of a mixture, such as an azeptrope, azeotropic composition or azeotrope-like composition, to facilitate the separation of the components thereof. The extractant interacts selectively with (but does not react with) one or more components within the mixture, and is typically introduced at an upper feed point of a distillation column, while the mixture requiring separation is introduced at the same, or preferably a relatively lower, feed point of the column than the extractant. The extractant passes downwardly through trays or packing located in the column and exits the column bottoms with one or more components of the mixture to be separated. While in the presence of the extractant, at least one of the components to be separated becomes relatively more volatile compared to the other components of the mixture, and the more volatile component of the initial mixture exits the column overhead.

A "fluorinated ionic liquid" is an ionic liquid having at least one fluorine on either the cation or the anion. A "fluorinated cation" or "fluorinated anion" is a cation or anion, respectively, comprising at least one fluorine.

A "fluorocarbon" or "fluorocarbon compound" is a compound comprising fluorine and carbon. A fluorocarbon or fluorocarbon compound may contain other atoms, such as chlorine or hydrogen.

A "high-boiling azeotrope" is an azeotrope, azeotropic composition or azeotrope-like composition that boils at a higher temperature at any given pressure than any one of the components therein would boil separately at that pressure. A high-boiling azeotrope may also be any azeotrope, azeotropic composition or azeotrope-like composition that has a lower vapor pressure at any given temperature than any one of the components therein would have separately at that temperature.

A "hydrofluorocarbon" or "hydrofluorocarbon compound" is a compound comprising fluorine, carbon, and at least one hydrogen atom.

A "halogen" is bromine, iodine, chlorine or fluorine atom.

A "heteroaryl" group is an aromatic group having a heteroatom.

A "heteroatom" is an atom other than carbon in the structure of an alkanyl, alkenyl or aromatic compound.

An "impurity" is a compound other than R-134 or R-134a in a mixture that contains R-134 and R-134a.

A "low-boiling-azeotrope" is an azeotrope, azeotropic composition or azeotrope-like composition that boils at a lower temperature at any given pressure than any one of the components therein would boil separately at that pressure. A low-boiling azeotrope may also be any azeotrope, azeotropic composition or azeotrope-like composition that has a higher vapor pressure at any given temperature than the vapor pressure of any one of the components therein would have separately at that temperature.

"Optionally substituted with at least one member selected from the group consisting of", when referring to an alkane, alkene, alkoxy, fluoroalkoxy, perfluoroalkoxy, fluoroalkyl, perfluoroalkyl, aromatic or heteroaryl radical or moiety, means that one or more hydrogens on a carbon chain of the radical or moiety may be independently substituted with one or more of the members of a recited group of substituents. For example, a substituted —$C_2H_5$ radical or moiety may, without limitation, be —$CF_2CF_3$, —$CH_2CH_2OH$ or —$CF_2CF_2I$ where the group or substituents consist of F, I and OH.

"Selectivity", $\alpha_{ij}$, with respect to components i and j in a mixture, is the ratio of the infinite dilution activity coefficient of component i to the infinite dilution activity coefficient of component j, component i and j being present at an infinite degree of dilution in the mixture as subjected to a separation process.

"Separating" or "to separate" refers to the removal of one or more components from a mixture. In various embodiments, separating or to separate may refer to the partial or complete removal of one or more components from a mixture. If purification is required, a series of separation steps may be required to achieve complete removal of a component. Subsequent separation steps, like initial separation steps, may be performed, for example, by processes such as distillation, gas stripping, chromatography and/or evaporation.

A "vacuum" is a pressure less than 1 bar but greater than $10^{-4}$ bar for practical use in extractive distillation equipment.

Because of their tendency to form an azeotrope, azeotropic composition or an azeotrope-like composition, R-134 and R-134a are extremely difficult to separate. An ionic liquid is therefore used to increase the efficiency of the separation of those components from a mixture thereof. An ionic liquid suitable for use herein to increase the efficiency of the separation of a mixture containing both R-134 and R-134a can in principle be any ionic liquid in which R-134 is more soluble than R-134a, or in which R-134a is more soluble than R-134. Preferably, to maximize separation efficiency, the ionic liquid should have high solubility for one of these two mixture components, thereby allowing for high-efficiency separation of the two components.

An ionic liquid, or a mixture of two or more thereof, may be used in a process hereof to facilitate the separation of R-134 and R-134a in a mixture thereof. Ionic liquids are organic compounds that are liquid at room temperature (approximately 25° C.). They differ from most salts in that they have very low melting points, and they generally tend to be liquid over a wide temperature range. They also generally tend to not be soluble in non-polar hydrocarbons; to be immiscible with water (depending on the anion); and to be highly ionizing (but have a low dielectric strength). Ionic liquids have essentially no vapor pressure, most are air and water stable, and they can either be neutral, acidic or basic.

A cation or anion of an ionic liquid useful herein can in principle be any cation or anion such that the cation and anion together form an organic salt that is liquid at or below about 100° C. The properties of an ionic liquid can, however, be tailored by varying the identity of the cation and/or anion. For example, the acidity of an ionic liquid can be adjusted by varying the molar equivalents and type and combinations of Lewis acids used.

Many ionic liquids are formed by reacting a nitrogen-containing heterocyclic ring, preferably a heteroaromatic ring, with an alkylating agent (for example, an alkyl halide) to form a quaternary ammonium salt, and performing ion exchange or other suitable reactions with various Lewis acids or their conjugate bases to form the ionic liquid. Examples of suitable heteroaromatic rings include substituted pyridines, imidazole, substituted imidazole, pyrrole and substituted pyrroles. These rings can be alkylated with virtually any straight, branched or cyclic $C_{1-20}$ alkyl group, but preferably, the alkyl groups are $C_{1-16}$ groups, since groups larger than this may produce low melting solids rather than ionic liquids. Various triarylphosphines, thioethers and cyclic and non-cyclic quaternary ammonium salts may also been used for this purpose. Counterions that may be used include chloroaluminate, bromoaluminate, gallium chloride, tetrafluoroborate, tetrachloroborate, hexafluorophosphate, nitrate, trifluoromethane sulfonate, methylsulfonate, p-toluenesulfonate, hexafluoroantimonate, hexafluoroarsenate, tetrachloroaluminate, tetrabromoaluminate, perchlorate, hydroxide anion, copper dichloride anion, iron trichloride anion, zinc trichloride anion, as well as various lanthanum, potassium, lithium, nickel, cobalt, manganese, and other metal-containing anions.

Ionic liquids may also be synthesized by salt metathesis, by an acid-base neutralization reaction or by quaternizing a selected nitrogen-containing compound; or they may be obtained commercially from several companies such as Merck (Darmstadt, Germany) or BASF (Mount Olive, N.J.).

Representative examples of useful ionic liquids are described in sources such as *J. Chem. Tech. Biotechnol.*, 68:351-356 (1997); *Chem. Ind.*, 68:249-263 (1996); *J. Phys. Condensed Matter*, 5: (supp 34B):B99-B106 (1993); *Chemical and Engineering News*, Mar. 30, 1998, 32-37; *J. Mater. Chem.*, 8:2627-2636 (1998); *Chem. Rev.*, 99:2071-2084 (1999); and US 2004/0133058 (which is incorporated as a part hereof). In one embodiment hereof, a library, i.e. a combinatorial library, of ionic liquids may be prepared, for example, by preparing various alkyl derivatives of a particular cation (such as the quaternary ammonium cation), and varying the associated anions.

In various different embodiments of this invention, an ionic liquid suitable for use may have a cation selected from those shown in the following formulae:

wherein $R^1$, $R^2$, $R^3$, $R^4$, $R^5$ and $R^6$ are independently selected from the group consisting of:

(i) H;
(ii) halogen;
(iii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
(iv) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
(v) $C_6$ to $C_{20}$ unsubstituted aryl, or $C_3$ to $C_{25}$ unsubstituted heteroaryl having one to three heteroatoms independently selected from the group consisting of O, N, Si and S; and
(vi) $C_6$ to $C_{25}$ substituted aryl, or $C_3$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:
  (1) —$CH_3$, —$C_2H_5$, or $C_3$ to $C_{25}$ straight-chain, branched or cyclic alkane or alkene, optionally substituted with at least one member selected from the group consisting of Cl, Br, F I, OH, $NH_2$ and SH,
  (2) OH,
  (3) $NH_2$, and
  (4) SH;
$R^7$, $R^8$, $R^9$ and $R^{10}$ are independently selected from the group consisting of:
  (vii) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH;
  (viii) —$CH_3$, —$C_2H_5$, or $C_3$ to $C_{25}$ straight-chain, branched or cyclic alkane or alkene comprising one to three heteroatoms selected from the group consisting of O, N, Si and S, and optionally substituted with at least one member selected from the group consisting of Cl, Br, F, I, OH, $NH_2$ and SH;
  (ix) $C_6$ to $C_{25}$ unsubstituted aryl, or $C_3$ to $C_{25}$ unsubstituted heteroaryl having one to three heteroatoms independently selected from the group consisting of O, N, Si and S; and
  (x) $C_6$ to $C_{25}$ substituted aryl, or $C_3$ to $C_{25}$ substituted heteroaryl having one to three heteroatoms independently selected from the group consisting of O, N, Si and S; and wherein said substituted aryl or substituted heteroaryl has one to three substituents independently selected from the group consisting of:
    (1) —$CH_3$, —$C_2H_5$, or $C_3$ to $C_{25}$ straight-chain, branched or cyclic alkane or alkene, optionally substituted with at least one member selected from the group consisting of Cl, Br, F, I, OH, $NH_2$ and SH,
    (2) OH,
    (3) $NH_2$, and
    (4) SH; and
wherein, optionally, at least two of $R^1$, $R^2$, $R^3$, $R^4$, $R^5$, $R^6$, $R^7$, $R^8$, $R^9$ and $R^{10}$ together form a cyclic or bicyclic alkanyl or alkenyl group.

In another embodiment, ionic liquids useful for this invention include fluorinated cations wherein at least one member selected from $R^1$, $R^2$, $R^3$, $R^4$, $R^5$, $R^6$, $R^7$, $R^8$, $R^9$ and $R^{10}$ comprises $F^-$.

In another embodiment, ionic liquids have anions selected from the group consisting of $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$; and preferably any fluorinated anions of the invention include $[BF_4]^-$, $[BF_3CF_3]^-$, $[BF_3C_2F_5]^-$, $[PF_6]^-$, $[PF_3(C_2F_5)_3]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_{21}CF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$; and $F^-$. In another embodiment, ionic liquids comprise a cation selected from the group consisting of pyridinium, pyridazinium, pyrimidinium, pyrazinium, imidazolium, pyrazolium, thiazolium, oxazolium, triazolium, phosphonium, and ammonium as defined above; and an anion selected from the group consisting of $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$; and any fluorinated anion. In yet another embodiment, ionic liquids comprise a cation selected from the group consisting of pyridinium, pyridazinium, pyrimidinium, pyrazinium, imidazolium, pyrazolium, thiazolium, oxazolium, triazolium, phosphonium, and ammonium as defined above; and an anion selected from the group consisting of $[BF_4]^-$, $[BF_3CF_3]^-$, $[BF_3C_2F_5]^-$, $[PF_6]^-$, $[PF_3(C_2F_5)_3]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, $[PF_3(C_2H_5)_3]^-$ and $F^-$.

In still another embodiment, ionic liquids comprise a cation selected from the group consisting of pyridinium, pyridazinium, pyrimidinium, pyrazinium, imidazolium, pyrazolium, thiazolium, oxazolium, triazolium, phosphonium, and ammonium as defined above, wherein at least one member selected from $R^1$, $R^2$, $R^3$, $R^4$, $R^5$, $R^6$, $R^7$, $R^8$, $R^9$, and $R^{10}$ comprises $F^-$; and an anion selected from the group consisting of $[CH_3CO_2]^-$, $[HSO_4]^-$, $[CH_3OSO_3]^-$, $[C_2H_5OSO_3]^-$, $[AlCl_4]^-$, $[CO_3]^{2-}$, $[HCO_3]^-$, $[NO_2]^-$, $[NO_3]^-$, $[SO_4]^{2-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$; and any fluorinated anion. In still another embodiment, ionic liquids comprise a cation selected from the group consisting of pyridinium, pyridazinium, pyrimidinium, pyrazinium, imidazolium, pyrazolium, thiazolium, oxazolium, triazolium, phosphonium, and ammonium as defined above, wherein at least one member selected from $R^1$, $R^2$, $R^3$, $R^4$, $R^5$, $R^6$, $R^7$, $R^8$, $R^9$, and $R^{10}$ comprises $F^-$; and an anion selected from the group consisting of $[BF_4]^-$, $[BF_3CF_3]^-$, $[BF_3C_2F_5]^-$, $[PF_6]^-$, $[PF_3(C_2F_5)_3]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, and $F^-$.

In a more specific embodiment, ionic liquids useful for the invention comprise:
a) imidazolium or pyridinium as the cation, and an anion selected from the group consisting of $[BF_4]^-$, $[BF_3CF_3]^-$, $[BF_3C_2F_5]^-$, $[PF_6]^-$, $[PF_3(C_2F_5)_3]^-$, $[SbF_6]^-$, $[CF_3SO_3]^-$, $[HCF_2CF_2SO_3]^-$, $[CF_3HFCCF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$,

[CF₃CO₂]⁻, [CF₃OCFHCF₂SO₃]⁻, [CF₃CF₂OCFHCF₂SO₃]⁻, [CF₃CFHOCF₂CF₂SO₃]⁻, [CF₂HCF₂OCF₂CF₂SO₃]⁻, [CF₂ICF₂OCF₂CF₂SO₃]⁻, [CF₃CF₂OCF₂CF₂SO₃]⁻, [(CF₂HCF₂SO₂)₂N]⁻, [(CF₃CFHCF₂SO₂)₂N]⁻, [CH₃OSO₃]⁻;

b) 1-butyl-3-methylimidazolium as the cation, and an anion selected from the group consisting of [BF₄]⁻, [BF₃CF₃]⁻, [BF₃C₂F₅]⁻, [PF₆]⁻, [PF₃(C₂F₅)₃]⁻, [SbF₆]⁻, [CF₃SO₃]⁻, [HCF₂CF₂SO₃]⁻, [CF₃HFCCF₂SO₃]⁻, [HCClFCF₂SO₃]⁻, [(CF₃SO₂)₂N]⁻, [(CF₃CF₂SO₂)₂N]⁻, [(CF₃SO₂)₃C]⁻, [CF₃CO₂]⁻, [CF₃OCFHCF₂SO₃]⁻, [CF₃CF₂OCFHCF₂SO₃]⁻, [CF₃CFHOCF₂CF₂SO₃]⁻, [CF₂HCF₂OCF₂CF₂SO₃]⁻, [CF₂ICF₂OCF₂CF₂SO₃]⁻, [CF₃CF₂OCF₂CF₂SO₃]⁻, [(CF₂HCF₂SO₂)₂N]⁻, [(CF₃CFHCF₂SO₂)₂N]⁻;

c) 1-ethyl-3-methylimidazolium as the cation, and an anion selected from the group consisting of [BF₄]⁻, [BF₃CF₃]⁻, [BF₃C₂F₅]⁻, [PF₆]⁻, [PF₃(C₂F₅)₃]⁻, [SbF₆]⁻, [CF₃SO₃]⁻, [HCF₂CF₂SO₃]⁻, [CF₃HFCCF₂SO₃]⁻, [HCClFCF₂SO₃]⁻, [(CF₃SO₂)₂N]⁻, [(CF₃CF₂SO₂)₂N]⁻, [(CF₃SO₂)₃C]⁻, and [CF₃CO₂]⁻, [CF₃OCFHCF₂SO₃]⁻, [CF₃CF₂OCFHCF₂SO₃]⁻, [CF₃CFHOCF₂CF₂SO₃]⁻, [CF₂HCF₂OCF₂CF₂SO₃]⁻, [CF₂ICF₂OCF₂CF₂SO₃]⁻, [CF₃CF₂OCF₂CF₂SO₃]⁻, [(CF₂HCF₂SO₂)₂N]⁻, [(CF₃CFHCF₂SO₂)₂N]⁻;

d) 1-ethyl-3-methylimidazolium as the cation, and [(CF₃CF₂SO₂)₂N]⁻, [PF₆]⁻, and [HCF₂CF₂SO₃]⁻ as the anion;

e) 1,3-dimethylimidazolium as the cation, and an anion selected from the group consisting of [BF₄]⁻, [BF₃CF₃]⁻, [BF₃C₂F₅]⁻, [PF₆]⁻, [PF₃(C₂F₅)₃]⁻, [SbF₆]⁻, [CF₃SO₃]⁻, [HCF₂CF₂SO₃]⁻, [CF₃HFCCF₂SO₃]⁻, [HCClFCF₂SO₃]⁻, [(CF₃SO₂)₂N]⁻, [(CF₃CF₂SO₂)₂N]⁻, [(CF₃SO₂)₃C]⁻, and [CF₃CO₂]⁻, [CF₃OCFHCF₂SO₃]⁻, [CF₃CF₂OCFHCF₂SO₃]⁻, [CF₃CFHOCF₂CF₂SO₃]⁻, [CF₂HCF₂OCF₂CF₂SO₃]⁻, [CF₂ICF₂OCF₂CF₂SO₃]⁻, [CF₃CF₂OCF₂CF₂SO₃]⁻, [(CF₂HCF₂SO₂)₂N]⁻, [(CF₃CFHCF₂SO₂)₂N]⁻;

(f) 3-methyl-1propylpyridinium as the cation and [(CF₃SO₂)₂N]⁻ as the anion; and (g) 1-hexyl-3-methylimidazolium as the cation and [PF₃(C₂F₅)₃]⁻ as the anion.

In various other embodiments of this invention, an ionic liquid formed by selecting any of the individual cations described or disclosed herein, and by selecting any of the individual anions described or disclosed herein, may be used for the purpose of effecting the separation of either R-134 or R-134a as a component from a mixture in which it is contained. Correspondingly, in yet other embodiments, a subgroup of ionic liquids formed by selecting (i) a subgroup of any size of cations, taken from the total group of cations described and disclosed herein in all the various different combinations of the individual members of that total group, and (ii) a subgroup of any size of anions, taken from the total group of anions described and disclosed herein in all the various different combinations of the individual members of that total group, may be used for the purpose of effecting the separation of either R-134 or R-134a as a component from a mixture in which it is contained. In forming an ionic liquid, or a subgroup of ionic liquids, by making selections as aforesaid, the ionic liquid or subgroup will be used in the absence of the members of the group of cations and/or anions that are omitted from the total group thereof to make the selection, and, if desirable, the selection may thus be made in terms of the members of the total group that are omitted from use rather than the members of the group that are included for use.

Systems of particular interest in this invention are those in which either R-134 or R-134a is separated as a component from a mixture in which it is contained with the other isomer by the addition to the mixture of at least one fluorinated ionic liquid, such as an ionic liquid that has a fluorinated anion, a fluorinated cation or both, in view of what may be useful interactions between and/or among the various fluorinated species that may increase the solubility of either R-134 or R-134a in an ionic liquid.

R-134 and R-134a, in their separated and pure states, have normal boiling points of −19.59° C. (R-134) and −26.11° C. (R-134a), respectively. These close boiling points make efficient separation of R-134 and R-134a by conventional processes extremely difficult because of the tendency of those components to form an azeotrope, azeotropic composition or an azeotrope-like composition in a mixture. The processes of this invention are consequently needed to improve the efficiency of efforts made to separate the two isomers, and do so by contacting the mixture with at least one ionic liquid. This is advantageous because at least one of the isomeric components of the mixture will be less soluble in the ionic liquid than the other component(s), and preferably much less soluble. This difference in solubility facilitates the separation of the lower-solubility component from the mixture because when that component is removed, such as by volatilization, the more-soluble component will be removed to a more limited extent, and will preferably not be removed at all, because to the extent that it is soluble in the ionic liquid, it will tend to remain in, and not be removed from, the mixture.

The separation processes of this invention may be performed, for example, by a technique such as extractive distillation. In extractive distillation, as in conventional distillation, the use of temperature and pressure control enables the volatilization of at least one individual component in a mixture, and the volatilized component(s) is captured in a separate stream in which it is condensed apart from, and is thus removed from, the mixture. In extractive distillation, however, there is added to the mixture a miscible, high boiling, relatively nonvolatile component, the extractant, that has low latent heat of vaporization, does not form an azeotrope with any of the components in the mixture, and does not chemically react with any of the components in the mixture. The extractant is specially chosen to interact differently with the various components of the mixture, thereby altering their relative volatilities and "breaking" any azeotrope, azeotropic composition or azeotrope-like composition in which they would otherwise exist. The extractant is chosen to be a substance in which one or more of the components of the mixture is more soluble, and preferably much more soluble, than at least one other component of the mixture. A component that is less soluble in the extractant may, as a result, be more easily volatilized and separated from the mixture than a component that is more soluble in the extractant. The tendency that the components of an azeotrope, azeotropic composition or azeotrope-like composition would ordinarily have to volatilize in the essentially the same compositional ratio as they possess in liquid from is thus altered by the presence in the mixture of the extractant, which, by solubilizing at least one component of the mixture to a greater extent than at least one other component, causes a corresponding change in the compositional content of the stream of volatiles liberated from the mixture at a selected temperature and pressure. The component(s) that are caused to be more volatile than others by the presence of the extractant in the mixture are then removed from the mixture as vapor in much higher concentration than the other components at the selected temperature and pressure. The more soluble, less volatile component(s) remain in the mixture with the extractant, and another criterion for selection of the extractant is that it be a substance that is easily separated from the remaining high-solubility, low-volatility component(s) of the mixture.

In various embodiments, it may be desirable to evaluate as the extractant a substance that causes the lower-boiling of two components in a mixture to become the more volatile of the two components as well. For example, a substance having greater chemical similarity to the higher-boiling of two components than to the lower-boiling may be evaluated for use as the extractant in such an embodiment. In various other embodiments, criteria that may be considered in evaluating a substance for selection as an extractant is whether the substance causes a positive deviation from Raoult's law with the lower-boiling of two components, or causes a negative deviation from Raoult's law with the higher-boiling of the two components.

When the separation process of this invention is performed by extractive distillation, an ionic liquid is used as an extractant. Mixtures of extractants, and thus mixtures of ionic liquids as extractants, may also be useful for achieving a desired extent of separation. In one embodiment, a mixture of extractants may be selected wherein one extractant has a high selectivity for the higher-volatility of the two components, and the other extractant has a high capacity to solubilize that component. In another embodiment, a mixture of ionic liquids may be used to separate the components of a mixture comprising at least two hydrofluorocarbon compounds by using multiple, discrete separation steps.

Figure 1:
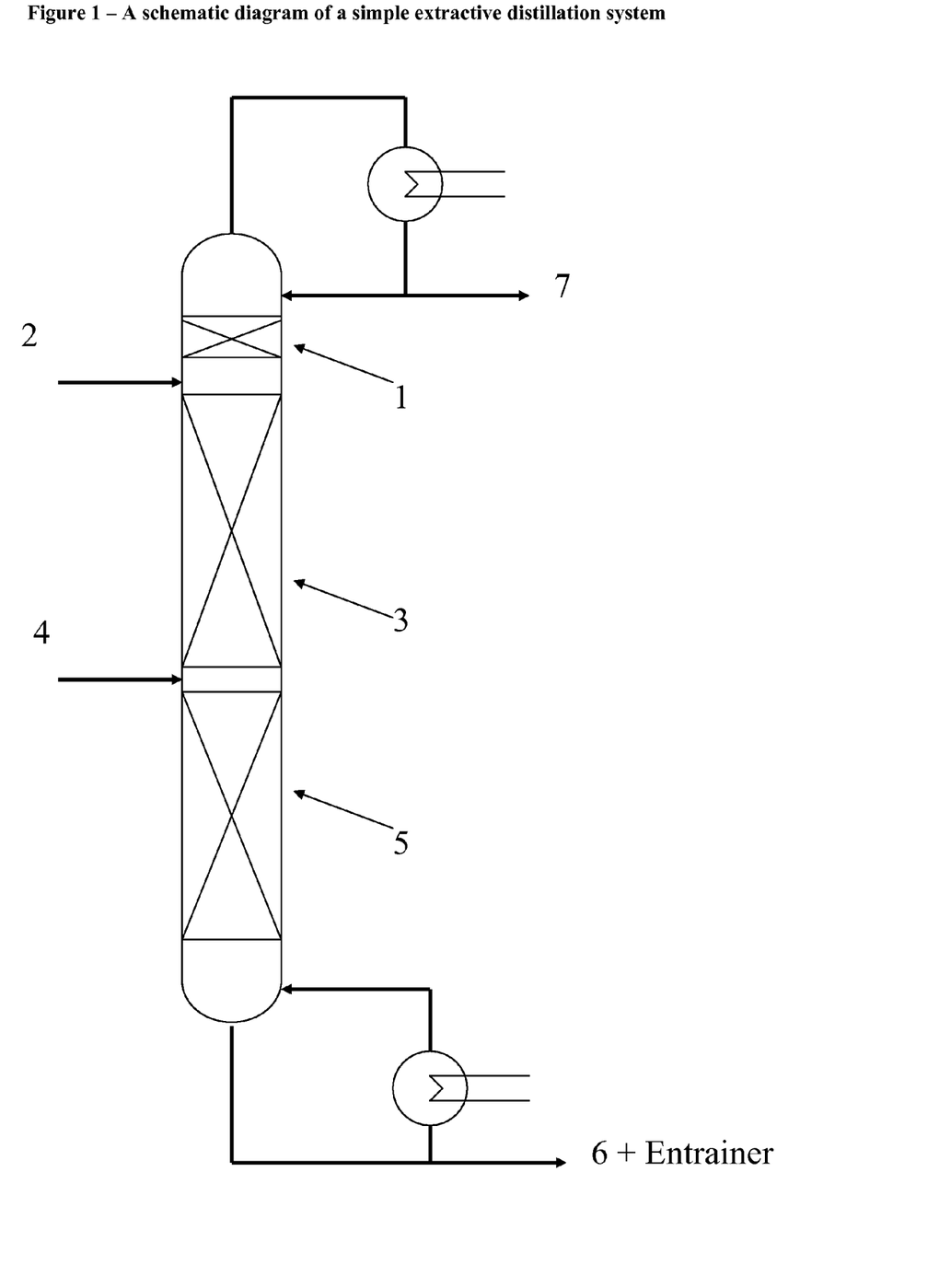
FIG. 1 shows a process schematic of an extractive distillation process.

When the separation process of this invention is performed by extractive distillation, it may be advantageously performed in a distillation column such as is shown in the schematic diagram of FIG. 1. In the column of FIG. 1, separator elements 1 are used for the separation from the extractant of the top product, which is the mixture component that is made more volatile (less soluble) by the presence of the extractant in the mixture. Use of an ionic liquid as the extractant has the advantage of essentially eliminating the presence of the extractant in the overhead product 7 because of what is typically the negligible volatility of an ionic liquid. The overhead or distillate stream exiting the column may be condensed using reflux condensers. At least a portion of this condensed stream can be returned to the top of the column as reflux, and the remainder recovered as product or for optional processing. The ratio of the condensed material that is returned to the top of the column as reflux to the material removed as distillate is commonly referred to as the reflux ratio. In extractive distillation, the extractant exits from the bottom of the column along with at least one mixture component that is more soluble in the ionic liquid. These may be sent to a second separation step where the extractant and a more soluble component are separated and recovered. The extractant may be recycled to the extractive distillation column for reuse.

The flow of the extractant enters at inlet 2, which is preferably located in the enriching section close to the top of the column below the condenser, or at the bottom of the rectifying section, wherein any amount of the extractant that has unexpectedly volatilized is separated from the higher-volatility, less-soluble component of the mixture. The ionic liquid as extractant then proceeds in a countercurrent flow direction downward in the column relative to the upward flow of the higher-volatility component, and perhaps other components of the mixture to be separated. The mixture enters at inlet 4, above the stripping section, where any of the higher-volatility component that is still admixed with the extractant is finally vaporized. The inlet feed of the mixture to be separated may be in liquid or gaseous form, and, if the mixture is in liquid form when fed into the column, the higher-volatility component(s) thereof will be volatilized by the temperature and pressure conditions of the column, which will have been selected for that purpose. The vapors rising in the column are continuously enriched in content of the higher-volatility, less-soluble component of the mixture, and the liquid moving downward in the column is continuously depleted in content of that higher-volatility component.

Separator elements 3 and 5 contain a useful number of stages along the height of the column at which there is thorough gas-liquid contacting, which is desirable for the purpose of obtaining extensive separation of a higher-volatility, less-soluble component, which exits the column as the overhead product 7, from a lower-volatility, more-soluble component, which exits the column together with the extractant as the bottom product 6. Separator elements can be either plates, or ordered or disordered packings. In either event, the purpose is to provide a downward cascade of the liquid extractant to contact the rising stream of vaporized high-volatility component. If plates are used, the liquid may flow over the edge of one plate onto another, or the liquid may flow through the same holes in the plates through which the volatilized component rises. In either case, the objective is to achieve maximum residence time of gas-liquid contact consistent with providing a rate of upward vapor flow that is high enough to prevent the column from being flooded by the downcoming liquid, but is not so high that the vapor is pushed out of the column without sufficient time to contact the liquid.

There is, in terms of the amount of the mixture to be separated, a minimum amount of the extractant that is needed to "break" any azeotrope, azeotropic composition or azeotrope-like composition that may exist, and enable the separation of at least one of the components from the mixture from the others in a yield and at a rate that is commercially feasible. In a ratio of the amount of extractant to the amount of feed, where the amount of extractant used in the ratio is the minimum amount described above, the value of the ratio may be set, for example, in the range of about 2 to about 4. Although feed ratios above 5 are sometimes found to offer no particular advantage in terms of being able to reduce the number of stages in a column, higher or lower feed ratios may be used herein as circumstances dictate such as a molar ratio of extractant to feed in the range of about 0.1 to about 25.

The extractant is then removed from the mixture together with the lower-volatility, more-soluble component in a separate step, and is recycled to the column for re-entry into the column at inlet 2. The extractant may be separated from the bottom product 6 using various separating operations including regeneration by simple evaporation. Thin film evaporators, such as falling-film or rotary evaporators, are commonly used for continuous evaporation. In discontinuous concentration processes, two evaporator stages are run alternately so that regenerated ionic liquid, as extractant, can be returned continuously to the distillation column. The extractant can also be regenerated by means of a stripping column since the vapor pressure of the ionic liquid is essentially zero. An alternative means of recovering an ionic liquid as extractant takes advantage of the fact that many ionic liquids can solidify below 0° C. In these cases, low cost separation of the ionic liquid can be achieved by cooling to form a solid phase. The bottom product can also be precipitated using techniques such as cooling, evaporative, or vacuum crystallization.

These and other aspects of extractive distillation are further discussed in well-known sources such as *Perry's Chemical Engineers'Handbook*, 7$^{th}$ Ed. (Section 13, "Distillation", McGraw-Hill, 1997).

When the separation process of this invention is performed by extractive distillation, more than one distillation column may be required in systems in which a mixture contains multiple components to be separated. For example, non-close-boiling components may be separated and removed from the mixture using a first distillation column, and an azeotrope, azeotropic composition or azeotrope-like composition can then be separated using a second distillation column. An ionic liquid may be used as an extractant for one or both of the distillation columns. For example, where it is desirable to separate either R-134 or R-134a using one ionic liquid, one of the components may be recovered from the top of the column whereas the second component and ionic liquid can be recovered from the bottom of the column. The mixture comprising the second component and the ionic liquid can then be separated using a second distillation column (or flash tank); the second component can be recovered from the top of the second column (or flash tank), and the ionic liquid can be recovered from the bottom of the column (or flash tank) and recycled back to the first distillation column.

When the separation process of this invention is performed by extractive distillation, the individual components of the mixture to be separated may have respective concentrations ranging from about 0.05 to about 99.95 mole percent relative to the total weight of all components in the mixture plus the extractant depending on their location at any particular time in the column, at which location and time they may be subjected to a temperature in the range of from the reboiler temperature to the condenser temperature, and a pressure in the range of from vacuum to the critical pressure.

Extractive distillation processes operate at varying feed, reboiler, and condenser temperatures depending on the appropriate conditions for optimum separation. A typical extractive distillation process might operate with a condenser and/or feed composition chilled by water to a temperature of 5 to 10° C., or chilled by brine or ethylene glycol to even lower temperatures of 0 to −40° C. In some cases, if the extractive distillation column operates at close to the normal boiling point of a compound at about 1 atmosphere pressure, the feed and/or the condenser may cool the gas to even lower temperatures of −40 to −80° C. The reboiler can operate over a wide temperature range depending on the operating pressure of the column and the identity of the compound(s) being separated, which in the case of a fluorinated compound could be a temperature range of from about −80 to about 240° C. The operating pressure of the distillation system may range from about −100 kPa to about 3.45 MPa, and is typically about 101.3 kPa to about 2.76 MPa. Typically, an increase in the extractant feed rate relative to the feed rate of the mixture to be separated causes an increase in the purity of the product to be recovered with regard to those compound(s) being removed. The molar ratio of the extractant feed rate relative to the feed rate of the mixture to be separated may range from about 0.1 to about 25, and typically ranges from about 1 to about 10. Normally, increasing the reflux ratio results in increased distillate stream purity. Generally, the reflux ratio ranges between 1/2 to 200/1. The temperature of the condenser, if present, which is located adjacent to the top of the column, is normally either sufficient to substantially fully condense the distillate that is exiting from the top of the column, or is that temperature required to achieve the desired reflux ratio by partial condensation.

Figure 2:
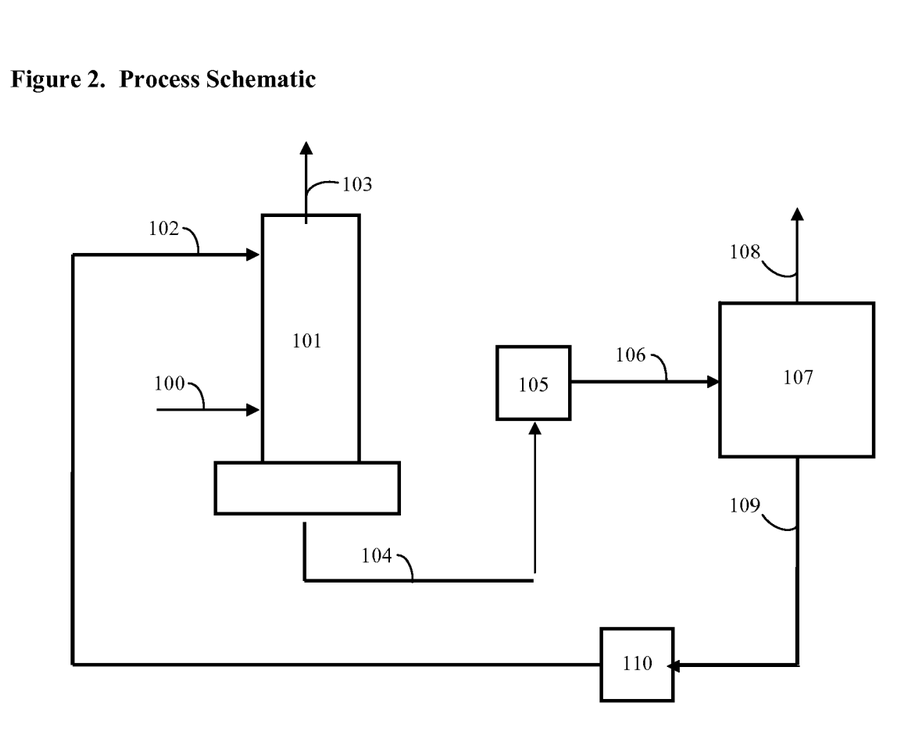
FIG. 2 shows a process schematic of an extractive distillation process.

Referring now to FIG. 2, there is shown a process flow diagram of an extractive distillation system for separating R-134a from a mixture comprising both R-134 and R-134a wherein the extractant is at least one ionic liquid in which R-134 is more soluble than R-134a, such as 1-ethyl-3-methylimidazolium bis(trifluoromethylsulfonyl)imide ([emim][Tf$_2$N]. Use of an ionic liquid as the extractant has the advantage of having essentially no extractant loss in the overhead product due to its negligible volatility; therefore it may not be necessary to have any separation stages above the extractant feed point. The feed mixture comprising R-134 and R-134a is supplied via conduit 100 typically to an intermediate location in extractive distillation column 101. The extractant comprising at least one ionic liquid is supplied via conduit 102 to the extractive distillation column 101 at a feed point (i.e., separation stage) higher in the column than the feed point of the 134/134a mixture. The overhead distillate 103 from column 101 contains concentrated R-134a, reduced in R-134 relative to the feed mixture, and essentially free of the extractant (<0.1%). A stream comprising the extractant and R-134, reduced in R-134a relative to the feed mixture, is removed from the bottom of column 101 via conduit 104 and transported to optional equipment 105 capable of heating or cooling and/or increasing or reducing the stream pressure.

Optional equipment 105 may be a heat exchanger, a pump, a valve, and/or any other devices for accomplishing the temperature, pressure, and/or phase change of a material stream. From optional equipment 105, the material stream comprising the extractant and R-134 substantially free of R-134a is transported via conduit 106 to extractant recovery unit 107. Extractant recovery unit 107 separates the stream comprising the ionic liquid extractant and R-134 into an R-134 stream essentially free of the extractant, which is removed via conduit 108, and an extractant stream substantially free of R-134 and R-134a that is removed via conduit 109 and transported to optional equipment 110 and from there optionally returned via conduit 102 to extractive distillation column 101 as the extractant stream. Extractant recovery unit 107 can consist of any separation method capable of separating a low-boiling compound from an extractant comprising an essentially non-volatile ionic liquid. Such separation methods include stripping, especially stripping in the presence of a gas (e.g. air or nitrogen) or a condensable vapor (e.g. steam), provided that the gas or vapor does not adversely interact with the low-boiling compound or ionic liquid, flashing at elevated temperature and/or reduced pressure, evaporation, especially falling-film or wiped-film evaporation.

An alternative means of recovering the ionic liquid takes advantage of the fact that many ionic liquids solidify below 0° C. In these cases, separation of the ionic liquid can be achieved by cooling to form a solid phase. The ionic liquid is obtained in solid form leaving behind the purified R-134. Optional equipment 110 may be a heat exchanger, pump, valve, and/or any other devices for accomplishing the temperature, pressure, and/or phase change of a material stream. The R-134 stream essentially free of the extractant, which is removed via conduit 108.

Impurities present in the feed mixture or in the separated R-134 or R-134a streams (i.e., stream 108 and stream 103, respectively) can be separated using one or more additional separation steps (not shown). The one or more additional separation steps can be placed prior to the extractive distillation column wherein R-134 or R-134a is separated from the mixture, or can be placed after said extractive distillation column as appropriate. Whether or not any impurities present in these streams will need to be separated will depend on the use of the product to be obtained by this process.

A process similar to that described as above and in FIG. 2 can also be used to separate R-134 from a mixture comprising both R-134 and R-134a by selecting an ionic liquid for carrying out an extractive distillation using the techniques as described above. Separated R-134 and/or R-134a streams can be partially or completely recovered as a liquid or as a vapor by conventional means.

For example, in one embodiment of a process as provided herein, (a) a mixture of R-134 and R-134a may be contacted with an ionic liquid to form a second mixture, (b) the second mixture may be processed by distillation, (c) R-134 may be recovered as a distillation-column overhead stream, and (d) R-134a and an ionic liquid may be recovered as a distillation-column bottom stream. Conversely, in another embodiment, (a) a mixture of R-134 and R-134a may be contacted with an ionic liquid to form a second mixture, (b) the second mixture may be processed by distillation, (c) R-134a may be recovered as a distillation-column overhead stream, and (d) R-134 and an ionic liquid may be recovered as a distillation-column bottom stream.

The ease of separation for a binary mixture of two components i and j by distillation can be determined by their relative volatility. The larger the relative volatility difference, the easier the separation. For mixtures with a small relative volatility, extractive distillation may be used to make the separation easier. In extractive distillation, the extractant influences the separation by selectively interacting with one or more of the components in the mixture. The selectivity for a binary mixture composed of i and j is defined as the ratio of the infinite dilution activity coefficient of compound i to the infinite dilution activity coefficient of compound j, where compounds i and j are present at an infinite degree of dilution in the extractant. The further the selectivity is from the value of one, the easier it is for the compounds of the mixture to be separated by extractive distillation. In general, the selectivity can be greater than or less than 1.0 depending on whether the more volatile or less volatile compound is in the numerator and depending on how the extractant modifies the volatility of the two compounds. Normally the more volatile compound is placed in the numerator and the selectivity has a value greater than 1.0, although in some cases the value can be less than 1.0. The selectivity ratio for components in a mixture is further discussed in sources such as *Kirk-Othmer Encyclopedia of Chemical Technology*, 5$^{th}$ Edition, Volume 13, pages 242-281 (2005) John Wiley & Sons, Inc., Hoboken, N.J. In order to achieve any practical amount of separation, a selectivity of greater than or less than 1.0 is required. In one embodiment of the processes of this invention, the selectivity is greater than about 1.9 to about 2.3.

The following examples are presented to illustrate the advantages of this invention and to assist one of ordinary skill in making and using the same. These examples are not intended in any way to limit the scope of the invention. The operation of the invention is illustrated by data related to the solubility of R-134 and R-134a in various ionic liquids. In this work, selectivities such as are described in Example 1 were used to determine the extent to which R-134 and R-134a could be separated. Example 2 uses a process simulation program (Aspen Plus™; Aspen Technology, Inc., Version 13.2, Cambridge, Mass.) to model the separation of R-134a and R-134 by extractive distillation using 1-ethyl-3-methylimidazolium bis(trifluoromethylsulfonyl)imide ([emim][Tf$_2$N]) as the extractant.

General Methods and Materials

The following nomenclature and abbreviations are used:
C=concentration (mol·m$^{-3}$)
C$_b$=buoyancy force (N)
C$_f$=correction factor (kg)
C$_0$=initial concentration (mol·m$^{-3}$)
C$_s$=saturation concentration (mol·m$^{-3}$)
<C>=space-averaged concentration (mol·m$^{-3}$)
D=diffusion constant (m$^2$·s$^{-1}$)
g=gravitational acceleration (9.80665 m·s$^{-2}$)
L=length (m)
m$_a$=mass absorbed (kg)
m$_i$=mass of i-th species on sample side of balance (kg)
m$_j$=mass of j-th species on counterweight side of balance (kg)
m$_{IL}$=mass of ionic liquid sample (kg)
MW$_i$=molecular weight of i-th species (kg·mol$^{-1}$)
N=n-th number component
P=pressure (MPa)
P$_0$=initial pressure (MPa)
t=time (s)
T$_{ci}$=critical temperature of i-th species (K)
T$_i$=temperature of i-th species (K)
T$_j$=temperature of j-th species (K)
T$_s$=temperature of sample (K)
V$_i$=volume of i-th species (m$^3$)
V$_{IL}$=volume of ionic liquid (m$^3$)
V$_m$=liquid sample volume (m$^3$)
$\tilde{V}_g$=molar volume of gas (m$^3$·mol$^{-1}$)
$\tilde{V}_i$=molar volume of i-th species (m$^3$·mol$^{-1}$)
$\tilde{V}_{IL}$=molar volume of ionic liquid (m$^3$·mol$^{-1}$)
$\tilde{V}_m$=molar volume of mixture (m$^3$·mol$^{-1}$)
$\tilde{V}_0$=initial molar volume (m$^3$·mol$^{-1}$)
Δ$\tilde{V}$=change in molar volume (m$^3$·mol$^{-1}$)
x$_i$=mole fraction of i-th species
z=depth (m)
λ$_n$=eigenvalue (m$^{-1}$)
ρ$_g$=density of gas (kg·m$^{-3}$)
ρ$_i$=density of i-th component on sample side of balance (kg·m$^{-3}$)
ρ$_j$=density of j-th component on counter weight side of balance (kg·m$^{-3}$)
ρ$_{air}$=density of air (kg·m$^{-3}$)
ρ$_s$=density of sample (kg·m$^{-3}$)
Units
Pa≡Pascal
MPa≡Mega Pascal
kPa≡kilopascal
mol≡mole
m≡meter
cm≡centimeter
K≡Kelvin
N≡Newton
J≡Joule
kJ≡kilojoule
kg≡kilogram
g≡gram
mg≡milligram
μg≡microgram
T=temperature
P=pressure
mbar≡millibar
h or hr≡hour
min≡minute
° C.≡degrees Centigrade
sec≡second
kW≡kilowatt
kg/s≡kilogram per second
kg/hr≡kilogram per hour 1-Butyl-3-methylimidazolium hexafluorophosphate ([bmim][PF$_6$], 1-ethyl-3-methylimidazolium bis(trifluoromethylsulfonyl)imide ([emim][Tf$_2$N] and 3-methyl-1-propylpyridinium bis(trifluoromethylsulfonyl)imide ([pmpy][Tf$_2$N] were obtained from Fluka Chemika (may be obtained from Sigma-Aldrich, St. Louis, Mo.) with a purity of >97%. 1-Hexyl-3-methylimidazolium tris(pentafluoroethyl)trifluorophosphate [hmim][PF$_3$(C$_2$F$_5$)$_3$] was obtained from Merck & Co. (Gibbstown, N.J.).

R-134 (CHF$_2$CHF$_2$, molecular weight 102 g mol$^{-1}$, normal boiling point $-19.6°$ C.), R-134a (CH$_2$FCF$_3$, molecular weight 102 g mol$^{-1}$, normal boiling point $-26.1°$ C.), R-114 (CClF$_2$CClF$_2$, molecular weight 170.9 g mol$^{-1}$, normal boiling point 3.6° C.), R-114a (CCl$_2$FCF$_3$ molecular weight 170.9 g mol$^{-1}$, normal boiling point 3.0° C.), R-124 (CClHFCF$_3$, molecular weight 136.5 g mol$^{-1}$, normal boiling point $-12.0°$ C.), and R-124a (CHF$_2$CClF$_2$ molecular weight 136.5 g mol$^{-1}$, normal boiling point $-10.2°$ C.) were obtained from DuPont Fluorochemicals (Wilmington, Del.), with a minimum purity of 99%.

The R-134, R-134a, R-114, R-114a, R-124, and R-124a solubility measurements were made using a gravimetric microbalance (IGA 003, Hiden Isochema Ltd., Warrington, UK). The microbalance consists of an electrobalance with sample and counterweight components inside a stainless steel pressure-vessel. The balance has a weigh range of 0-100 mg with a resolution of 0.1 µg. An enhanced pressure stainless steel (SS316LN) reactor capable of operation to 2.0 MPa and 100° C. was installed. Approximately 60 mg of ionic liquid sample was added to the sample container and the reactor was sealed. The sample was dried and degassed by first pulling a coarse vacuum on the sample with a diaphragm pump (Pfeiffer, model MVP055-3, Asslar, Germany) and then fully evacuating the reactor to $10^{-9}$ MPa with a turbopump (Pfeiffer, model TSH-071). While under deep vacuum, the sample was heated to 75° C. for 10 h with an external water jacket connected to a remote-controlled constant-temperature bath (Huber Ministat, model cc-S3, Offenburg, Germany). A 30 percent ethylene glycol and 70 percent water mixture by volume was used as the recirculating fluid with a temperature range of 5 to 90° C. The sample mass slowly decreased as residual water and gases were removed. Once the mass had stabilized for at least 60 min, the sample dry mass was recorded.

The IGA003 can operate in both dynamic and static mode. Dynamic mode operation provides a continuous flow of gas (maximum 500 cm$^3$ min$^{-1}$) past the sample, and the exhaust valve controls the set-point pressure. Static mode operation introduces gas into the top of the balance away from the sample and both the admittance and exhaust valves control the set-point pressure. All absorption measurements were performed in static mode.

The sample temperature was measured with a type K thermocouple with an accuracy of ±0.1° C. The thermocouple was located inside the reactor next to the sample container. The water jacket maintained the set-point temperature automatically to within a typical regulation accuracy of ±0.1° C. Four isotherms (at 10, 25, 50, and 75° C.) were measured beginning with 10° C.

Once the desired temperature was achieved and stable, the admittance and exhaust valves opened and closed as necessary to adjust the pressure to the first set-point. Pressures from $10^{-10}$ to $10^{-2}$ MPa were measured using a capacitance manometer (Pfeiffer, model PKR251), and pressures from $10^{-2}$ to 2.0 MPa were measured using a piezo-resistive strain gauge (Druck, model PDCR4010, New Fairfield, Conn.). Regulation maintained the reactor pressure set-point to within ±4 to 8 kPa. The pressure ramp rate was set at 200 kPa min$^{-1}$ and the temperature ramp rate was set at 1° C. min$^{-1}$. The upper pressure limit of the stainless steel reactor was 2.0 MPa, and several isobars (i.e. 0.1, 0.5, 1, 2, 3 MPa) were measured. To ensure sufficient time for gas-liquid equilibrium, the ionic liquid samples were maintained at set-point for a minimum of 3 h with a maximum time-out of 12 h. Additional details of the experimental equipment and procedures have been published (M. B. Shiflett and A. Yokozeki, *Ind. Eng. Chem. Res.* (2005) 44(12), 4453-4464).

EXAMPLE 1

Separation of 1,1,2,2-tetrafluoroethane (R-134) and 1,1,1,2-tetrafluoroethane (R-134a)

This example focuses on the thermodynamic properties at the infinite dilution state. Activity coefficients at infinite dilution $\gamma^\infty$ were analyzed for R-134 and R-134a in [bmim][PF$_6$] and [emim][Tf$_2$N].

Experimental solubility (PTx) data for R-134 and R-134a in [bmim][PF$_6$] and [emim][Tf$_2$N] are summarized in Examples 3 and 4 for [bmim][PF$_6$] and Examples 5 and 10 for [emim][Tf$_2$N]. Data have been correlated with the Non-Random-Two-Liquid (NRTL) solution model. The NRTL (S. I., Sandler, Chemical and Engineering Thermodynamics, 3$^{rd}$ Edition (1999) John Wiley and Sons, Inc., New York, Chapter 7) activity coefficient ($\gamma_i$) model for a binary system is given by:

$$\ln\gamma_1 = x_2^2\left[\tau_{21}\left(\frac{G_{21}}{x_1+x_2G_{21}}\right)^2 + \frac{\tau_{12}G_{12}}{(x_2+x_1G_{12})^2}\right], \quad (1)$$

$$\ln\gamma_2 = x_1^2\left[\tau_{12}\left(\frac{G_{12}}{x_2+x_1G_{12}}\right)^2 + \frac{\tau_{21}G_{21}}{(x_1+x_2G_{21})^2}\right], \quad (2)$$

where $$G_{12} \equiv \exp(-\alpha\tau_{12}), \text{ and } G_{21} \equiv \exp(-\alpha\tau_{21}), \quad (3)$$

$$\tau_{12} \text{ and } \tau_{21}: \text{adjustable binary interaction parameters.} \quad (4)$$

$\alpha = 0.2$ (assumed to be a constant of 0.2 in this work). The temperature-dependent binary interaction parameter ($\tau_{ij}$) is modeled by:

$$\tau_{ij} = \tau_{ij}^{(0)} + \tau_{ij}^{(1)}/T. \quad (5)$$

Vapor liquid equilibria (VLE) are obtained by solving the following equations:

$$y_i P \Phi_i = x_i \gamma_i P_i^S, \text{ (i=1 for R-134 or R-134a and i=2 for ionic liquid)} \quad (6)$$

In the present system, it was assumed that $P_2^S \approx 0$ and $y_2 \approx 0$ (or $y_1 \approx 1$). Thus, eq 6 becomes only one equation with i=1, and the correction factor for vapor-phase non-ideality, $\Phi_1$, can be written as:

$$\Phi_1 = \exp\left[\frac{(B_{11}-\overline{V_1})(P-P_1^S)}{RT}\right]. \quad (7)$$

The second virial coefficient, $B_{11}(T)$, of pure species 1 can be calculated with proper equation-of-state models, and the saturated molar liquid volume, $\overline{V}_1(T)$, is calculated using the method described in Shiflett, M. B. and Yokozeki, A. (Solubility and Diffusivity of Hydrofluorocarbons in Room-Temperature Ionic Liquids. *AIChE J.* (2006), 52, 1205). The vapor pressure of pure species 1 is modeled by:

$$\log_{10} P_1^S = A_1 - \frac{B_1}{T + C_1}. \quad (8)$$

The coefficients in eq 8 for R-134 are ($A_1$=7.810141, $B_1$=2306.21, $C_1$=−25.3612) and R-134a are ($A_1$=8.10384, $B_1$=2432.86, $C_1$=−12.3310), and it was assumed that eq 8 holds even above VLE (vapor liquid equilibrium) critical temperature $T_c$ as an extrapolated hypothetical vapor pressure.

The present solubility model contains a maximum of four adjustable parameters: $\tau_{12}^{(0)}$, $\tau_{12}^{(1)}$, $\tau_{21}^{(0)}$, and $\tau_{21}^{(1)}$. These parameters have been determined using non-linear least-squares analysis with an objective function of: $\Sigma_{i=1}^{N}(1-P_{obs}(i)/P_{calc}(i))^2$ for N data points. Optimal values for these parameters for R-134 in [bmim][PF$_6$] are $\tau_{12}^{(0)}$=8.63198, $\tau_{12}^{(1)}$=−2228.072 K, $\tau_{21}^{(0)}$=−2.89313, and $\tau_{21}^{(1)}$=551.474 K. Optimal values for these parameters for R-134a in [bmim][PF$_6$] are $\tau_{12}^{(0)}$=2.92373, $\tau_{12}^{(1)}$=192.105 K, $\tau_{21}^{(0)}$=−0.50499, and $\tau_{21}^{(1)}$=−251.738 K. Optimal values for these parameters for R-134 in [emim][Tf$_2$N] are $\tau_{12}^{(0)}$=3.23841, $\tau_{12}^{(1)}$=−1641.731 K, $\tau_{21}^{(0)}$=−5.24746, and $\tau_{21}^{(1)}$=2460.150 K. Optimal values for these parameters for R-134a in [emim][Tf$_2$N] are $\tau_{12}^{(0)}$=−1.41623, $\tau_{12}^{(1)}$=1466.520 K, $\tau_{21}^{(0)}$=1.20533, and $\tau_{21}^{(1)}$=−838.522 K.

Although the infinite dilution state is only a limited (or extrapolated) state of actual solutions, the thermodynamic properties at such a state provide important physiochemical understandings about solute and solvent interactions. Activity coefficients at infinite dilution, $\gamma_1^\infty$, of R-134 and R-134a in [bmim][PF$_6$] can be derived from eq 1 by setting $x_1$=0 and $x_2$=1.

$$\ln \gamma_1^\infty = \tau_{21} + \tau_{12} G_{12}. \quad (9)$$

Table 1 provides the temperature (T), the saturated vapor pressure ($P_i^S$), the $2^{nd}$ virial coefficient ($B_{11}$), and the activity coefficient at infinite dilution ($\gamma_1^\infty$) for R-134 and R-134a in [bmim][PF$_6$].

TABLE 1

| Gas | Ionic Liquid | T (C.) | $P_i^S$ (MPa) | $B_{11}$ (cm$^3$ mol$^{-1}$) | $\gamma_1^\infty$ |
|---|---|---|---|---|---|
| R-134a | [bmim][PF$_6$] | 10 | 0.415 | −566.51 | 1.431 |
| R-134a | [bmim][PF$_6$] | 25 | 0.665 | −493.66 | 1.490 |
| R-134a | [bmim][PF$_6$] | 50 | 1.317 | −398.96 | 1.579 |
| R-134a | [bmim][PF$_6$] | 75 | 2.363 | −328.12 | 1.659 |
| R-134 | [bmim][PF$_6$] | 10 | 0.322 | −478.80 | 0.748 |
| R-134 | [bmim][PF$_6$] | 25 | 0.525 | −433.71 | 0.883 |
| R-134 | [bmim][PF$_6$] | 50 | 1.062 | −369.23 | 1.042 |
| R-134 | [bmim][PF$_6$] | 75 | 1.933 | −315.40 | 1.127 |
| R-134a | [emim][Tf$_2$N] | 10 | 0.415 | −566.51 | 1.017 |
| R-134a | [emim][Tf$_2$N] | 25 | 0.665 | −493.66 | 1.140 |
| R-134a | [emim][Tf$_2$N] | 50 | 1.317 | −398.96 | 1.326 |
| R-134a | [emim][Tf$_2$N] | 75 | 2.363 | −328.12 | 1.485 |
| R-134 | [emim][Tf$_2$N] | 10 | 0.322 | −478.80 | 0.436 |
| R-134 | [emim][Tf$_2$N] | 25 | 0.525 | −433.71 | 0.568 |
| R-134 | [emim][Tf$_2$N] | 50 | 1.062 | −369.23 | 0.743 |
| R-134 | [emim][Tf$_2$N] | 75 | 1.933 | −315.40 | 0.847 |

These activity coefficients at infinite dilution $\gamma_1^\infty$ were used to calculate the selectivity ($\alpha_{ij}$):

$$\alpha_{ij} = \frac{\gamma_i^\infty}{\gamma_j^\infty}$$

where components i and j are present at an infinite degree of dilution in the extractant [bmim][PF$_6$] or [emim][Tf$_2$N], and i represents R-134a, and j represents R-134. In order to achieve separation, a selectivity of greater than or less than 1.0 is required. The selectivities ($\alpha_{ij}$) in Tables 2a and 2b show that the use of [bmim] [PF$_6$] as an extractant will separate R-134a and R-134 with a selectivity of greater than 1.5 to 1.9 over a temperature range from 10 to 75° C. The selectivities ($\alpha_{ij}$) in Table 2 show that the use of [emim][Tf$_2$N] as an extractant will separate R-134a and R-134 with a selectivity of greater than 1.7 to 2.3 over a temperature range from 10 to 75° C.

TABLE 2a

Selectivity for R-134a (i) and R-134 (j) in [bmim][PF$_6$]

| T (C.) | $\gamma_i^\infty$ | $\gamma_j^\infty$ | $\alpha_{ij}$ |
|---|---|---|---|
| 10 | 1.431 | 0.748 | 1.91 |
| 25 | 1.490 | 0.883 | 1.69 |
| 50 | 1.579 | 1.042 | 1.52 |
| 75 | 1.659 | 1.127 | 1.47 |

TABLE 2b

Selectivity for R-134a (i) and R-134 (j) in [emim][Tf$_2$N]

| T (C.) | $\gamma_i^\infty$ | $\gamma_j^\infty$ | $\alpha_{ij}$ |
|---|---|---|---|
| 10 | 1.017 | 0.436 | 2.33 |
| 25 | 1.140 | 0.568 | 2.01 |
| 50 | 1.326 | 0.743 | 1.78 |
| 75 | 1.485 | 0.847 | 1.75 |

EXAMPLE 2

Separation of a Mixture Comprising 1,1,1,2 Tetrafluoroethane and 1,1,2,2 Tetrafluoroethane The Aspen Plus™ (Aspen Technology, Inc., Version 13.2, Cambridge, Mass.) process simulator was used to model the separation of a mixture comprising of 1,1,1,2 tetrafluoroethane (also known as HFC-134a or R-134a) and 1,1,2,2 tetrafluoroethane (also known as HFC-134 or R-134) by extractive distillation using [emim][Tf$_2$N] as the extractant.

The ionic liquid was treated as non-dissociating liquid with a very low vapor pressure. The nonrandom two-liquid (NRTL) activity coefficient model (S. I., Sandler, Chemical and Engineering Thermodynamics, 3 Edition (1999) John Wiley and Sons, Inc., New York, Chapter 7) was used to model the liquid phase interactions between the ionic liquid and the fluorocarbon compounds and the Peng-Robinson equation of state was used to model the vapor phase. Binary NRTL interaction parameters for the ionic liquid with the fluorocarbons R-134, R-134a, R-114, R-114a, R-124, and R-124a were regressed from (P, T, x) data obtained from solubility experiments. (See Examples 5 and 10 to 14 for the solubility data.)

In this modeled example, 100 lb/hr (45.36 kg/hr) of a mixture of composition 66.08 wt % R-134a, 31.74 wt % R-134, 0.11 wt % R-114, 130 ppm R-114a, 1.89 wt % R-124, and 0.17 wt % R-124a is fed to an extractive distillation column containing 32 theoretical stages and operating at 54.7 psia (377 kPa) with a reflux ratio of 3.0. This fluorocarbon feed, at a temperature of about 12° C., is fed on the $13^{th}$ stage from the top of the column. The extractant stream, with a composition of 99.5 wt % of the ionic liquid [emim][Tf$_2$N], 0.49 wt % R-134, and 110 ppm of R-124, is fed at 0° C. to the second stage from the top of the extractive distillation column. The mass flowrate of the extractant stream is controlled at approximately 4.0 times the mass flowrate of the fluorocarbon feed.

As seen in Table 3 below, at these conditions, 99.7% of the R-134a in the fluorocarbon feed is recovered in the extractive distillation column distillate at a purity of 99.0 wt %. In addition, the distillate also contains 0.61 wt % R-134, all of the chlorofluorocarbons (R-114 and R-114a) and about 6% of the hydrochlorofluorocarbons (R-124 and R-124a) present in the original feed mixture. About 98.8% of the R-134 in the fluorocarbon feed leaves from the bottom of the extractive distillation column along with the ionic liquid extractant and the remaining fraction of R-124 and R-124a. The temperatures at the top and bottom of the extractive distillation column are 7.2 and 80.7° C., respectively.

The bottoms stream from the extractive distillation column is reduced in pressure across a valve (labeled 105 in FIG. 1) to 17.7 psia (122 kPa), causing partial vaporization of the stream, and fed to a wiped-film evaporator (labeled 107 in FIG. 1). Because the viscosity of [emim][Tf$_2$N] is not too high, a standard falling-film evaporator, could have been used instead. The wiped-film evaporator operates at 17.7 psia (122 kPa) and produces a vapor stream (labeled as 108 in FIG. 1) containing 98.7% of the R-134 in the original fluorocarbon feed mixture. This stream has a composition of 93.66 wt % R-134, 5.29 wt % R-124, 0.59 wt % R-134a, 0.47 wt % R-124a, and nondetectible amounts of the ionic liquid [emim][Tf$_2$N]. Essentially all of the ionic liquid [emim][Tf$_2$N] leaves as the concentrate from the wiped-film evaporator. One way to keep the temperature of this stream reasonable is to allow some amount of fluorocarbon to remain with the non-volatile [emim][Tf$_2$N]. For this example, 0.50 wt %, essentially all R-134, remains in the recovered [emim][Tf$_2$N]. The recovered ionic liquid stream is cooled and pumped to higher pressure (both steps are represented by block 110 in FIG. 1) and then returned to the extractive distillation column as the extractant feed stream.

Examples 3 and 4 provide solubility results for 1,1,2,2-tetrafluoroethane (R-134) and 1,1,1,2-tetrafluoroethane (R-134a) in [bmim][PF$_6$], respectively. These data are used for calculating the activity coefficient at infinite dilution ($\gamma_1^\infty$) as shown in Example 1.

EXAMPLE 3

Solubility of 1,1,2,2-tetrafluoroethane (R-134) in 1-butyl-3-methylimidazolium hexafluorophosphate [bmim] [PF$_6$]

A solubility study was made at temperatures of about 10 to 75° C. over a pressure range from 0.1 bar (0.01 MPa) to about 3.5 bar (0.35 MPa) where the solubilities (x) or mole fractions of R-134 in [bmim][PF$_6$] were measured using a gravimetric microbalance. Table 4 provides data for T, P, and x, respectively.

TABLE 4

| T (° C.) | P (bar) | R-134 (mole fraction) |
|---|---|---|
| 10.01 | 0.10 | 0.029 |
| 9.97 | 0.50 | 0.176 |
| 9.99 | 1.00 | 0.357 |
| 9.99 | 1.50 | 0.528 |
| 9.97 | 2.00 | 0.686 |
| 9.98 | 2.50 | 0.814 |
| 9.96 | 3.00 | 0.974 |
| 25.02 | 0.10 | 0.024 |
| 24.93 | 0.50 | 0.116 |
| 24.89 | 1.00 | 0.225 |
| 24.93 | 1.50 | 0.330 |
| 24.92 | 2.00 | 0.428 |
| 25.00 | 2.50 | 0.522 |
| 24.90 | 3.00 | 0.611 |
| 24.94 | 3.50 | 0.689 |
| 49.97 | 0.10 | 0.006 |
| 49.97 | 0.50 | 0.049 |
| 49.99 | 1.00 | 0.103 |
| 50.01 | 1.50 | 0.155 |
| 49.98 | 2.00 | 0.205 |

TABLE 3

Aspen Plus ™ Simulation Results

| | Stream Number: | | | | | | |
|---|---|---|---|---|---|---|---|
| | 100 | 102 | 103 | 104 | 106 | 108 | 109 |
| Mass Flow Rates: kg/hr | | | | | | | |
| R-114 | 0.0515 | 0.0000 | 0.0515 | 0.0000 | 0.0000 | 0.0000 | 0.0000 |
| R-114a | 0.0061 | 0.0000 | 0.0061 | 0.0000 | 0.0000 | 0.0000 | 0.0000 |
| R-124 | 0.8577 | 0.0203 | 0.0554 | 0.8225 | 0.8225 | 0.8022 | 0.0203 |
| R-124a | 0.0758 | 0.0020 | 0.0044 | 0.0733 | 0.0733 | 0.0713 | 0.0020 |
| R-134 | 14.3954 | 0.8642 | 0.1854 | 15.0743 | 15.0743 | 14.2100 | 0.8642 |
| R-134a | 29.9728 | 0.0016 | 29.8837 | 0.0907 | 0.0907 | 0.0891 | 0.0016 |
| [emim][Tf$_2$N] | 0.0000 | 176.5853 | 0.0000 | 176.5853 | 176.5853 | 0.0000 | 176.5853 |
| Mass Fractions | | | | | | | |
| R-114 | 0.0011 | 0.0000 | 0.0017 | 0.0000 | 0.0000 | 0.0000 | 0.0000 |
| R-114a | 0.0001 | 0.0000 | 0.0002 | 0.0000 | 0.0000 | 0.0000 | 0.0000 |
| R-124 | 0.0189 | 0.0001 | 0.0018 | 0.0043 | 0.0043 | 0.0529 | 0.0001 |
| R-124a | 0.0017 | 0.0000 | 0.0001 | 0.0004 | 0.0004 | 0.0047 | 0.0000 |
| R-134 | 0.3174 | 0.0049 | 0.0061 | 0.0782 | 0.0782 | 0.9366 | 0.0049 |
| R-134a | 0.6608 | 0.0000 | 0.9900 | 0.0005 | 0.0005 | 0.0059 | 0.0000 |
| [emim][Tf$_2$N] | 0.0000 | 0.9950 | 0.0000 | 0.9166 | 0.9166 | 0.0000 | 0.9950 |
| Total Mass Flows: kg/hr | 45.3592 | 177.4734 | 30.1865 | 192.6462 | 192.6462 | 15.1727 | 177.4734 |

TABLE 4-continued

| T (° C.) | P (bar) | R-134 (mole fraction) |
|---|---|---|
| 50.00 | 2.50 | 0.255 |
| 49.97 | 3.00 | 0.302 |
| 50.01 | 3.50 | 0.346 |
| 74.93 | 0.10 | 0.006 |
| 75.01 | 0.50 | 0.029 |
| 74.99 | 1.00 | 0.058 |
| 75.01 | 1.50 | 0.087 |
| 74.99 | 2.00 | 0.114 |
| 75.01 | 2.50 | 0.141 |
| 75.00 | 3.00 | 0.167 |
| 74.99 | 3.50 | 0.196 |

EXAMPLE 4

Solubility of 1,1,1,2-tetrafluoroethane (R-134a) in 1-butyl-3-methylimidazolium hexafluorophosphate [bmim] [$PF_6$]

A solubility study was made at temperatures of about 10 to 75° C. over a pressure range from 0.1 bar (0.01 MPa) to about 3.5 bar (0.35 MPa) where the solubilities (x) or mole fractions of R-134a in [bmim][$PF_6$] were measured using a gravimetric microbalance. Table 5 provides data for T, P, and x, respectively.

TABLE 5

| T (° C.) | P (bar) | R134a (mole fraction) |
|---|---|---|
| 9.8 | 0.100 | 0.003 |
| 10.0 | 0.498 | 0.050 |
| 9.9 | 0.999 | 0.126 |
| 9.9 | 1.498 | 0.213 |
| 9.9 | 2.002 | 0.305 |
| 9.9 | 2.491 | 0.404 |
| 9.9 | 2.997 | 0.519 |
| 9.9 | 3.490 | 0.724 |
| 25.0 | 0.100 | 0.011 |
| 24.9 | 0.498 | 0.042 |
| 25.0 | 0.997 | 0.086 |
| 25.0 | 1.499 | 0.130 |
| 25.0 | 1.993 | 0.176 |
| 24.9 | 2.500 | 0.224 |
| 25.0 | 2.995 | 0.275 |
| 24.9 | 3.500 | 0.326 |
| 49.9 | 0.099 | 0.004 |
| 50.0 | 0.498 | 0.021 |
| 49.9 | 0.997 | 0.043 |
| 49.9 | 1.499 | 0.065 |
| 50.0 | 1.990 | 0.087 |
| 50.0 | 2.490 | 0.109 |
| 50.0 | 2.990 | 0.131 |
| 50.0 | 3.493 | 0.154 |
| 75.0 | 0.097 | 0.000 |
| 74.9 | 0.498 | 0.009 |
| 74.9 | 0.993 | 0.022 |
| 74.9 | 1.501 | 0.035 |
| 75.0 | 1.998 | 0.047 |
| 75.0 | 2.501 | 0.059 |
| 75.0 | 3.002 | 0.072 |
| 75.0 | 3.490 | 0.085 |

Additional examples 5 to 9 provide solubility results for 1,1,2,2-tetrafluoroethane (R-134) in several other ionic liquids which all work to varying degrees to separate R-134 from R-134a. A low viscosity ionic liquid with high solubility for R-134 is 1-ethyl-3-ethylimidazolium bis(trifluoromethylsulfonyl)imide ([emim][$Tf_2N$] or [emim][BMeI]). Solubility results for R-134 in [emim][$Tf_2N$] are shown in Example 5. This ionic liquid, [emim][$Tf_2N$], was also measured with R-134a (Example 10) and several of the impurities which can be present in the manufacturing to produce R-134/R-134a. These data are shown in Examples 11 to 14. The data in Examples 3, 4, 5, and 10 were used for calculating the activity coefficients and ideal selectivities in Example 1. Furthermore the data in Examples 5 and 10, along with the data found in Examples 11-14 for the solubility of R-114, R-114a, R-124, and R-124a were used for calculating the physical property parameters used in the Aspen Plus™ modeling in Example 2.

EXAMPLE 5

Solubility of 1,1,2,2-tetrafluoroethane (R-134) in 1-ethyl-3-methylimidazolium bis(trifluoromethylsulfonyl)imide [emim] [$Tf_2N$]

A solubility study was made at temperatures of about 10 to 75° C. over a pressure range from 0.1 bar (0.01 MPa) to about 3.5 bar (0.35 MPa) where the solubilities (x) or mole fractions of R-134 in [emim][$Tf_2N$] were measured using a gravimetric microbalance. Table 6 provides data for T, P, and x, respectively.

TABLE 6

| T (° C.) | P (bar) | R-134 (mole fraction) |
|---|---|---|
| 9.76 | 0.10 | 0.055 |
| 10.01 | 0.50 | 0.246 |
| 9.92 | 1.00 | 0.433 |
| 10.10 | 1.50 | 0.573 |
| 9.81 | 2.00 | 0.702 |
| 9.98 | 2.50 | 0.811 |
| 10.01 | 3.00 | 0.964 |
| 25.08 | 0.10 | 0.033 |
| 25.01 | 0.50 | 0.156 |
| 25.01 | 1.00 | 0.284 |
| 24.97 | 1.50 | 0.395 |
| 25.05 | 2.00 | 0.490 |
| 24.91 | 2.50 | 0.573 |
| 24.90 | 2.99 | 0.648 |
| 25.02 | 3.50 | 0.716 |
| 49.90 | 0.10 | 0.016 |
| 49.94 | 0.50 | 0.076 |
| 50.01 | 1.00 | 0.147 |
| 49.93 | 1.51 | 0.210 |
| 49.91 | 2.00 | 0.269 |
| 49.87 | 2.49 | 0.323 |
| 49.94 | 3.00 | 0.374 |
| 49.94 | 3.50 | 0.421 |
| 74.98 | 0.10 | 0.006 |
| 74.94 | 0.50 | 0.040 |
| 74.95 | 1.01 | 0.079 |
| 74.92 | 1.50 | 0.116 |
| 74.91 | 2.00 | 0.152 |
| 74.93 | 2.50 | 0.186 |
| 74.94 | 3.00 | 0.219 |
| 74.95 | 3.50 | 0.250 |

EXAMPLE 6

Solubility of 1,1,2,2-tetrafluoroethane (R-134) in 3-methyl-1-propylpyridinium bis(trifluoromethylsulfonyl)imide [pmpy] [$Tf_2N$]

A solubility study was made at temperatures of about 10 to 75° C. over a pressure range from 0.1 bar (0.01 MPa) to about 3.5 bar (0.35 MPa) where the solubilities (x) or mole fractions of R-134 in [pmpy][$Tf_2N$] were measured using a gravimetric microbalance. Table 7 provides data for T, P, and x, respectively.

TABLE 7

| T (° C.) | P (bar) | R-134 (mole fraction) |
| --- | --- | --- |
| 9.85 | 0.10 | 0.058 |
| 9.93 | 0.50 | 0.258 |
| 9.96 | 1.00 | 0.442 |
| 9.87 | 1.50 | 0.584 |
| 10.03 | 1.99 | 0.697 |
| 9.98 | 2.50 | 0.803 |
| 9.97 | 2.99 | 0.925 |
| 24.99 | 0.10 | 0.035 |
| 24.99 | 0.50 | 0.161 |
| 24.92 | 1.00 | 0.292 |
| 24.87 | 1.50 | 0.403 |
| 24.91 | 2.00 | 0.496 |
| 25.04 | 2.49 | 0.574 |
| 25.07 | 3.00 | 0.645 |
| 25.00 | 3.49 | 0.711 |
| 50.05 | 0.10 | 0.018 |
| 49.93 | 0.50 | 0.081 |
| 49.94 | 1.00 | 0.154 |
| 49.94 | 1.50 | 0.219 |
| 49.94 | 2.00 | 0.279 |
| 49.94 | 2.50 | 0.334 |
| 49.86 | 2.99 | 0.385 |
| 49.87 | 3.50 | 0.432 |
| 74.94 | 0.10 | 0.005 |
| 74.94 | 0.50 | 0.040 |
| 74.97 | 1.00 | 0.082 |
| 74.91 | 1.50 | 0.122 |
| 74.98 | 2.00 | 0.160 |
| 74.99 | 2.50 | 0.196 |
| 74.93 | 3.00 | 0.230 |
| 74.92 | 3.50 | 0.262 |

EXAMPLE 7

Solubility of 1,1,2,2-tetrafluoroethane (R-134) in 1-hexyl-3-methylimidazolium tris(pentafluoroethyl) trifluorophosphate [hmim] [PF$_3$(C$_2$F$_5$)$_3$]

A solubility study was made at temperatures of about 10 to 75° C. over a pressure range from 0.1 bar (0.01 MPa) to about 3.5 bar (0.35 MPa) where the solubilities (x) or mole fractions of R-134 in [hmim][PF$_3$(C$_2$F$_5$)$_3$] were measured using a gravimetric microbalance. Table 8 provides data for T, P, and x, respectively.

TABLE 8

| T (° C.) | P (bar) | R-134 (mole fraction) |
| --- | --- | --- |
| 9.93 | 0.10 | 0.055 |
| 9.92 | 0.50 | 0.240 |
| 9.98 | 1.00 | 0.422 |
| 10.02 | 1.50 | 0.568 |
| 9.95 | 2.00 | 0.689 |
| 9.97 | 2.49 | 0.810 |
| 9.98 | 2.99 | 0.959 |
| 24.98 | 0.10 | 0.035 |
| 24.93 | 0.50 | 0.160 |
| 25.05 | 1.00 | 0.293 |
| 24.87 | 1.50 | 0.403 |
| 24.96 | 1.99 | 0.498 |
| 25.02 | 2.50 | 0.583 |
| 24.99 | 3.00 | 0.656 |
| 24.91 | 3.50 | 0.727 |
| 49.97 | 0.10 | 0.018 |
| 49.94 | 0.50 | 0.085 |
| 49.95 | 1.00 | 0.161 |
| 49.95 | 1.50 | 0.229 |
| 49.94 | 2.00 | 0.291 |
| 50.04 | 2.50 | 0.347 |
| 49.98 | 3.00 | 0.401 |
| 49.94 | 3.50 | 0.448 |

TABLE 8-continued

| T (° C.) | P (bar) | R-134 (mole fraction) |
| --- | --- | --- |
| 74.92 | 0.10 | 0.009 |
| 74.91 | 0.50 | 0.047 |
| 74.99 | 1.00 | 0.092 |
| 74.98 | 1.50 | 0.135 |
| 74.968 | 2.00 | 0.176 |
| 74.96 | 2.50 | 0.213 |
| 74.99 | 3.00 | 0.250 |
| 74.98 | 3.49 | 0.284 |

EXAMPLE 8

Solubility of 1,1,2,2-tetrafluoroethane (R-134) in 1,2-dimethyl-3-propylimidazolium tris(trifluoromethylsulfonyl)methide [dmpim] [TMeM]

A solubility study was made at temperatures of about 10 to 75° C. over a pressure range from 0.1 bar (0.01 MPa) to about 3.5 bar (0.35 MPa) where the solubilities (x) or mole fractions of R-134 in [dmpim][TMeM] were measured using a gravimetric microbalance. Table 9 provides data for T, P, and x, respectively.

TABLE 9

| T (° C.) | P (bar) | R-134 (mole fraction) |
| --- | --- | --- |
| 10.11 | 0.10 | 0.054 |
| 9.97 | 0.50 | 0.252 |
| 9.88 | 1.00 | 0.443 |
| 10.01 | 1.50 | 0.596 |
| 10.01 | 1.99 | 0.717 |
| 9.99 | 2.50 | 0.827 |
| 10.05 | 3.00 | 0.963 |
| 24.90 | 0.10 | 0.029 |
| 25.07 | 0.50 | 0.149 |
| 24.86 | 1.00 | 0.287 |
| 24.93 | 1.50 | 0.403 |
| 25.01 | 2.00 | 0.503 |
| 24.85 | 2.49 | 0.587 |
| 25.04 | 3.00 | 0.667 |
| 25.03 | 3.49 | 0.732 |
| 49.96 | 0.10 | 0.006 |
| 49.98 | 0.50 | 0.069 |
| 49.98 | 1.00 | 0.145 |
| 49.96 | 1.50 | 0.215 |
| 49.95 | 2.00 | 0.278 |
| 49.91 | 2.50 | 0.337 |
| 49.92 | 3.00 | 0.390 |
| 49.96 | 3.50 | 0.440 |
| 74.94 | 0.10 | 0.010 |
| 74.95 | 0.50 | 0.046 |
| 74.99 | 1.00 | 0.089 |
| 74.93 | 1.50 | 0.131 |
| 74.98 | 2.00 | 0.170 |
| 74.93 | 2.50 | 0.207 |
| 74.97 | 3.00 | 0.243 |
| 74.98 | 3.50 | 0.277 |

EXAMPLE 9

Solubility of 1,1,2,2-tetrafluoroethane (R-134) in 1-ethyl-3-methylimidazolium bis(pentafluoroethylsulfonyl)imide [emim] [BEI]

A solubility study was made at temperatures of about 10 to 75° C. over a pressure range from 0.1 bar (0.01 MPa) to about 3.5 bar (0.35 MPa) where the solubilities (x) or mole fractions of R-134 in [emim][BEI] were measured using a gravimetric microbalance. Table 10 provides data for T, P, and x, respectively.

TABLE 10

| T (° C.) | P (bar) | R-134 (mole fraction) |
|---|---|---|
| 9.999 | 0.10 | 0.039 |
| 9.973 | 0.50 | 0.236 |
| 9.982 | 1.00 | 0.430 |
| 9.999 | 1.50 | 0.584 |
| 9.973 | 2.00 | 0.708 |
| 9.999 | 2.50 | 0.823 |
| 10.042 | 3.00 | 0.980 |
| 25.062 | 0.10 | 0.038 |
| 25.004 | 0.50 | 0.169 |
| 25.004 | 1.00 | 0.305 |
| 25.037 | 1.50 | 0.417 |
| 24.978 | 2.00 | 0.518 |
| 24.995 | 2.50 | 0.606 |
| 25.079 | 3.00 | 0.677 |
| 24.953 | 3.50 | 0.735 |
| 49.998 | 0.11 | 0.019 |
| 50.023 | 0.50 | 0.086 |
| 49.998 | 1.00 | 0.162 |
| 49.99 | 1.50 | 0.232 |
| 49.99 | 2.00 | 0.295 |
| 49.982 | 2.50 | 0.355 |
| 49.982 | 3.00 | 0.407 |
| 49.998 | 3.49 | 0.460 |
| 75.014 | 0.11 | 0.010 |
| 74.998 | 0.50 | 0.048 |
| 74.982 | 1.00 | 0.094 |
| 74.973 | 1.50 | 0.136 |
| 75.006 | 2.00 | 0.176 |
| 75.006 | 2.50 | 0.215 |
| 75.014 | 3.00 | 0.293 |
| 74.99 | 3.50 | 0.371 |

EXAMPLE 10

Solubility of 1,1,1,2-tetrafluoroethane (R-134a) in 1-ethyl-3-methylimidazolium bis(trifluoromethylsulfonyl)imide [emim] [Tf$_2$N]

A solubility study was made at temperatures of about 10 to 75° C. over a pressure range from 0.1 bar (0.01 MPa) to about 3.5 bar (0.35 MPa) where the solubilities (x) or mole fractions of R-134a in [emim][Tf$_2$N] were measured using a gravimetric microbalance. Table 11 provides data for T, P, and x, respectively.

TABLE 11

| T (° C.) | P (bar) | R-134a (mole fraction) |
|---|---|---|
| 10.529 | 0.10 | 0.019 |
| 9.585 | 0.50 | 0.105 |
| 9.968 | 1.00 | 0.219 |
| 10.061 | 1.50 | 0.318 |
| 10.036 | 2.00 | 0.415 |
| 10.036 | 2.50 | 0.516 |
| 10.07 | 3.00 | 0.613 |
| 10.036 | 3.50 | 0.755 |
| 25.057 | 0.10 | 0.016 |
| 24.923 | 0.50 | 0.071 |
| 24.964 | 1.00 | 0.138 |
| 24.964 | 1.50 | 0.203 |
| 24.931 | 2.00 | 0.263 |
| 25.073 | 2.50 | 0.322 |
| 24.914 | 3.00 | 0.382 |
| 24.931 | 3.49 | 0.443 |
| 49.935 | 0.10 | 0.008 |
| 49.96 | 0.50 | 0.036 |
| 49.968 | 1.00 | 0.071 |
| 49.96 | 1.50 | 0.105 |
| 49.935 | 2.00 | 0.138 |
| 49.885 | 2.50 | 0.169 |
| 50.025 | 3.00 | 0.201 |
| 49.984 | 3.50 | 0.231 |
| 74.952 | 0.10 | 0.000 |
| 74.927 | 0.50 | 0.017 |
| 74.968 | 1.00 | 0.038 |
| 74.96 | 1.50 | 0.058 |
| 74.935 | 2.00 | 0.077 |
| 74.935 | 2.50 | 0.096 |
| 74.935 | 3.00 | 0.115 |
| 74.968 | 3.50 | 0.133 |

EXAMPLE 11

Solubility of 1,2-dichloro-1,1,2,2-tetrafluoroethane (R-114) in 1-ethyl-3-methylimidazolium bis(trifluoromethylsulfonyl)imide [emim] [Tf$_2$N]

A solubility study was made at temperatures of about 10 to 75° C. over a pressure range from 0.1 bar (0.01 MPa) to about 1.5 bar (0.15 MPa) where the solubilities (x) or mole fractions of R-114 in [emim][Tf$_2$N] were measured using a gravimetric microbalance. Table 12 provides data for T, P, and x, respectively.

TABLE 12

| T (° C.) | P (bar) | R-114 (mole fraction) |
|---|---|---|
| 9.976 | 0.10 | 0.012 |
| 9.874 | 0.50 | 0.060 |
| 9.9 | 0.75 | 0.092 |
| 9.9 | 1.00 | 0.126 |
| 24.881 | 0.10 | 0.006 |
| 25.073 | 0.50 | 0.034 |
| 25.157 | 0.70 | 0.050 |
| 24.923 | 1.00 | 0.073 |
| 25.006 | 1.25 | 0.093 |
| 24.931 | 1.50 | 0.113 |
| 49.877 | 0.10 | 0.004 |
| 49.976 | 0.50 | 0.018 |
| 49.968 | 0.71 | 0.026 |
| 49.984 | 1.00 | 0.036 |
| 49.918 | 1.25 | 0.045 |
| 49.91 | 1.50 | 0.055 |
| 74.952 | 0.10 | 0.000 |
| 74.968 | 0.50 | 0.009 |
| 74.984 | 0.71 | 0.013 |
| 74.976 | 1.00 | 0.019 |
| 74.944 | 1.25 | 0.024 |
| 74.952 | 1.50 | 0.030 |

EXAMPLE 12

Solubility of 1,1-dichloro-1,2,2,2-tetrafluoroethane (R-114a) in 1-ethyl-3-methylimidazolium bis(trifluoromethylsulfonyl)imide [emim] [Tf$_2$N]

A solubility study was made at temperatures of about 10 to 75° C. over a pressure range from 0.1 bar (0.01 MPa) to about 1.5 bar (0.15 MPa) where the solubilities (x) or mole fractions of R-114a in [emim][Tf$_2$N] were measured using a gravimetric microbalance. Table 13 provides data for T, P, and x, respectively.

TABLE 13

| T (° C.) | P (bar) | R-114a (mole fraction) |
| --- | --- | --- |
| 10.053 | 0.10 | 0.013 |
| 9.968 | 0.50 | 0.066 |
| 9.951 | 0.75 | 0.101 |
| 9.951 | 1.00 | 0.142 |
| 25.132 | 0.10 | 0.006 |
| 24.931 | 0.50 | 0.032 |
| 24.998 | 0.70 | 0.048 |
| 24.998 | 1.00 | 0.073 |
| 24.839 | 1.25 | 0.095 |
| 24.897 | 1.50 | 0.117 |
| 49.951 | 0.10 | 0.002 |
| 49.943 | 0.50 | 0.017 |
| 49.91 | 0.70 | 0.025 |
| 49.951 | 1.00 | 0.037 |
| 49.968 | 1.25 | 0.047 |
| 49.96 | 1.50 | 0.057 |
| 74.968 | 0.10 | 0.001 |
| 74.968 | 0.50 | 0.010 |
| 74.96 | 0.71 | 0.015 |
| 74.96 | 1.00 | 0.021 |
| 74.984 | 1.25 | 0.027 |
| 74.992 | 1.50 | 0.032 |

EXAMPLE 13

Solubility of 1-chloro-1,2,2,2-tetrafluoroethane (R-124) in 1-ethyl-3-methylimidazolium bis(trifluoromethylsulfonyl)imide [emim] [Tf$_2$N]

A solubility study was made at temperatures of about 10 to 75° C. over a pressure range from 0.1 bar (0.01 MPa) to about 3.0 bar (0.30 MPa) where the solubilities (x) or mole fractions of R-124 in [emim][Tf$_2$N] were measured using a gravimetric microbalance. Table 14 provides data for T, P, and x, respectively.

TABLE 14

| T (° C.) | P (bar) | R-124 (mole fraction) |
| --- | --- | --- |
| 9.883 | 0.10 | 0.050 |
| 10.027 | 0.50 | 0.224 |
| 9.934 | 1.00 | 0.422 |
| 9.942 | 1.50 | 0.591 |
| 9.985 | 2.00 | 0.757 |
| 24.914 | 0.10 | 0.028 |
| 25.015 | 0.50 | 0.134 |
| 24.872 | 1.00 | 0.259 |
| 25.04 | 1.50 | 0.369 |
| 24.923 | 2.00 | 0.473 |
| 25.048 | 2.50 | 0.568 |
| 24.99 | 3.00 | 0.665 |
| 49.993 | 0.10 | 0.010 |
| 49.951 | 0.50 | 0.058 |
| 49.976 | 1.00 | 0.115 |
| 49.96 | 1.50 | 0.169 |
| 49.976 | 2.00 | 0.221 |
| 49.951 | 2.50 | 0.272 |
| 49.943 | 3.00 | 0.322 |
| 74.96 | 0.10 | 0.001 |
| 74.984 | 0.50 | 0.026 |
| 74.976 | 1.00 | 0.057 |
| 74.976 | 1.50 | 0.088 |
| 74.952 | 2.00 | 0.118 |
| 74.968 | 2.50 | 0.145 |
| 74.927 | 3.00 | 0.171 |

EXAMPLE 14

Solubility of 1-chloro-1,1,2,2-tetrafluoroethane (R-124a) in 1-ethyl-3-methylimidazolium bis(trifluoromethylsulfonyl)imide [emim] [Tf$_2$N]

A solubility study was made at temperatures of about 10 to 75° C. over a pressure range from 0.1 bar (0.01 MPa) to about 3.0 bar (0.30 MPa) where the solubilities (x) or mole fractions of R-124a in [emim][Tf$_2$N] were measured using a gravimetric microbalance. Table 15 provides data for T, P, and x, respectively.

TABLE 15

| T (° C.) | P (bar) | R-124a (mole fraction) |
| --- | --- | --- |
| 10.044 | 0.10 | 0.047 |
| 9.968 | 0.50 | 0.212 |
| 9.934 | 1.00 | 0.401 |
| 9.959 | 1.50 | 0.573 |
| 9.985 | 2.00 | 0.759 |
| 24.964 | 0.10 | 0.029 |
| 25.065 | 0.50 | 0.128 |
| 24.964 | 1.00 | 0.244 |
| 24.973 | 1.50 | 0.356 |
| 24.822 | 1.99 | 0.461 |
| 24.998 | 2.50 | 0.572 |
| 24.948 | 3.00 | 0.692 |
| 49.894 | 0.10 | 0.012 |
| 49.894 | 0.50 | 0.058 |
| 50.034 | 1.00 | 0.116 |
| 50.025 | 1.50 | 0.171 |
| 49.935 | 2.00 | 0.222 |
| 49.935 | 2.50 | 0.271 |
| 49.96 | 3.00 | 0.322 |
| 74.927 | 0.10 | 0.001 |
| 74.919 | 0.50 | 0.027 |
| 74.935 | 1.00 | 0.057 |
| 74.968 | 1.50 | 0.087 |
| 74.895 | 2.00 | 0.116 |
| 74.927 | 2.50 | 0.143 |
| 74.952 | 3.00 | 0.171 |

What is claimed is:

1. A process for separating a member of the group (a) of components that consists of (i) 1,2-dichloro-1,1,2,2-tetrafluoroethane (R-114), (ii) 1,1-dichloro-1,2,2,2-tetrafluoroethane (R-114a), (iii) 1-chloro-1,2,2,2-tetrafluoroethane (R-124), (iv) 1-chloro-1,1,2,2-tetrafluoroethane (R-124a), and (v) a mixture of any two or more of the components (a)(i), (a)(ii), (a)(iii) and (a)(iv), from a combination of the group (a) component with a member of the group (b) of components that consists of (i) 1,1,2,2-tetrafluoroethane, (ii) 1,1,1,2-tetrafluoroethane and (iii) a mixture of both of the components (b)(i) and (b)(ii); comprising (I) contacting the combination of the group (a) component with the group (b) component with an ionic liquid that comprises a pyridinium cation or an imidazolium cation, and a fluorinated anion; (II) absorbing either the (b)(i) component or the (b)(ii) component into the ionic liquid; and (III) separating the ionic liquid and absorbed component from the combination.

2. A process according to claim 1 wherein a fluorinated anion comprises an anion selected from the group consisting of [BF$_4$]$^-$, [BF$_3$CF$_3$]$^-$, [BF$_3$C$_2$F$_5$]$^-$, [PF$_6$]$^-$, [PF$_3$(C$_2$F$_5$)$_3$]$^-$, [SbF$_6$]$^-$, [CF$_3$CO$_2$]$^-$, and F$^-$.

3. A process according to claim 1 wherein a fluorinated anion comprises an anion selected from the group consisting of [BF$_4$]$^-$, [BF$_3$CF$_3$]$^-$, [BF$_3$C$_2$F$_5$]$^-$, [PF$_6$]$^-$, [PF$_3$(C$_2$F$_5$)$_3$]$^-$, [SbF$_6$]$^-$, [CF$_3$SO$_3$]$^-$, [HCF$_2$CF$_2$SO$_3$]$^-$, [CF$_3$HFCCF$_2$SO$_3$]$^-$, [HCClFCF$_2$SO$_3$]$^-$, [(CF$_3$SO$_2$)$_2$N]$^-$, [(CF$_3$CF$_2$SO$_2$)$_2$N]$^-$, [(CF$_3$SO$_2$)$_3$C]$^-$, [CF$_3$CO$_2$]$^-$, [CF$_3$OCFHCF$_2$SO$_3$]$^-$,

[CF$_3$CF$_2$OCFHCF$_2$SO$_3$]$^-$, [CF$_3$CFHOCF$_2$CF$_2$SO$_3$]$^-$, [CF$_2$HCF$_2$OCF$_2$CF$_2$SO$_3$]$^-$, [CF$_2$ICF$_2$OCF$_2$CF$_2$SO$_3$]$^-$, [CF$_3$CF$_2$OCF$_2$CF$_2$SO$_3$]$^-$, [(CF$_2$HCF$_2$SO$_2$)$_2$N]$^-$, [(CF$_3$CFHCF$_2$SO$_2$)$_2$N]$^-$, and F$^-$.

4. A process according to claim 1 wherein a fluorinated anion comprises an anion selected from the group consisting of [CF$_3$SO$_3$]$^-$, [HCF$_2$CF$_2$SO$_3$]$^-$, [CF$_3$HFCCF$_2$SO$_3$]$^-$, [HCClFCF$_2$SO$_3$]$^-$, [CF$_3$OCFHCF$_2$SO$_3$]$^-$, [CF$_3$CF$_2$OCFHCF$_2$SO$_3$]$^-$, [CF$_3$CFHOCF$_2$CF$_2$SO$_3$]$^-$, [CF$_2$HCF$_2$OCF$_2$CF$_2$SO$_3$]$^-$, [CF$_2$ICF$_2$OCF$_2$CF$_2$SO$_3$]$^-$, and [CF$_3$CF$_2$OCF$_2$CF$_2$SO$_3$]$^-$.

5. A process according to claim 1 wherein a fluorinated anion comprises an anion selected from the group consisting of [(CF$_3$SO$_2$)$_2$N]$^-$, [(CF$_3$CF$_2$SO$_2$)$_2$N]$^-$, [(CF$_3$SO$_2$)$_3$C]$^-$, [(CF$_2$HCF$_2$SO$_2$)$_2$N]$^-$, and [(CF$_3$CFHCF$_2$SO$_2$)$_2$N]$^-$.

6. A process according to claim 1 wherein an ionic liquid comprises a 3-methyl-1-propylpyridinium cation, and a [(CF$_3$SO$_2$)$_2$N]$^-$ anion.

7. A process according to claim 1 which is performed in a distillation column.

8. A process according to claim 7 wherein an ionic liquid is fed to the column as an extractant and contacts the combination in the column.

9. A process according to claim 7 wherein a component (a) exits the top of the column as a vapor.

10. A process according to claim 7 wherein the combination comprise component (b)(iii), a mixture of both of the components (b)(i) and (b)(ii), and the non-absorbed member of component (b)(iii) exits the top of the column as a vapor.

11. A process according to claim 7 wherein the ratio of the moles of ionic liquid fed to the column to the moles of mixture to be separated fed to the column is in the range of from about 0.1 to about 25.

12. A process according to claim 7 wherein an ionic liquid is recovered from the column bottoms, the absorbed component is separated from the ionic liquid, and the ionic liquid is recycled to the column.

13. A process according to claim 1 wherein a cation is selected from the group consisting of a 1-butyl-3-methylimidazolium cation, a 1-ethyl-3-methylimidazolium cation, a 1,3-dimethylimidazolium cation, a 3-methyl-1propylpyridinium cation, and a 1-hexyl-3-methylimidazolium cation.

14. A process according to claim 1 wherein an ionic liquid comprises a 3-methyl-1-propylpyridinium cation, and an anion selected from the group consisting of hexafluorophosphate, bis(trifluoromethylsulfonyl)imide, tris(pentafluoroethyl)trifluorophosphate, tris(trifluoromethylsulfonyl)methide, and bis(pentafluoroethylsulfonyl)imide.

15. A process according to claim 1 wherein an ionic liquid comprises
  (i) a 1-butyl-3-methylimidazolium hexafluorophosphate cation, and an anion selected from the group consisting of bis(trifluoromethylsulfonyl)imide, tris(pentafluoroethyl)trifluorophosphate, tris(trifluoromethylsulfonyl)methide, and bis(pentafluoroethylsulfonyl)imide;
  (ii) 1-ethyl-3-methylimidazolium cation, and an anion selected from the group consisting of hexafluorophosphate, bis(trifluoromethylsulfonyl)imide, tris(pentafluoroethyl)trifluorophosphate, and tris(trifluoromethylsulfonyl)methide;
  (iii) 1-hexyl-3-methylimidazolium cation, and an anion selected from the group consisting of hexafluorophosphate, bis(trifluoromethylsulfonyl)imide, tris(pentafluoroethyl)trifluorophosphate, tris(trifluoromethylsulfonyl)methide, and bis(pentafluoroethylsulfonyl)imide; or
  (iv) 1,2-dimethyl-3-propylimidazolium cation, and an anion selected from the group consisting of hexafluorophosphate, bis(trifluoromethylsulfonyl)imide, tris(pentafluoroethyl)trifluorophosphate, tris(trifluoromethylsulfonyl)methide, and bis(pentafluoroethylsulfonyl)imide.

16. A process according to claim 1 wherein an ionic liquid comprises 1-ethyl-3-methylimidazolium bis(trifluoromethylsulfonyl)imide.

17. A process according to claim 7 wherein an ionic liquid exits the top of the column and is recovered, and the ionic liquid is recycled to the column.

18. A process according to claim 1 wherein the (b)(i) component is absorbed into the ionic liquid.

19. A process according to claim 1 wherein the (b)(ii) component is absorbed into the ionic liquid.

* * * * *